US009345716B2

(12) United States Patent
Banerjee et al.

(10) Patent No.: US 9,345,716 B2
(45) Date of Patent: May 24, 2016

(54) PROTEIN FREE SURFACTANT COMPOSITION FOR PULMONARY DISEASES AND A PROCESS FOR PREPARING THE SAME

(75) Inventors: Rinti Banerjee, Mumbai (IN); Anubhav Kaviratna, Mumbai (IN)

(73) Assignee: INDIAN INSTITUTE OF TECHNOLOGY, BOMBAY, Mumbai (IN)

( * ) Notice: Subject to any disclaimer, the term of this patent is extended or adjusted under 35 U.S.C. 154(b) by 333 days.

(21) Appl. No.: 13/992,571

(22) PCT Filed: Oct. 4, 2011

(86) PCT No.: PCT/IN2011/000691

§ 371 (c)(1),
(2), (4) Date: Aug. 21, 2013

(87) PCT Pub. No.: WO2012/077127

PCT Pub. Date: Jun. 14, 2012

(65) Prior Publication Data

US 2013/0323318 A1 Dec. 5, 2013

(30) Foreign Application Priority Data

Dec. 10, 2010 (IN) .................................... 3370/2010

(51) Int. Cl.

| | |
|---|---|
| ***A61K 31/662*** | (2006.01) |
| ***A61K 45/06*** | (2006.01) |
| ***A61K 31/085*** | (2006.01) |
| ***A61K 9/127*** | (2006.01) |
| ***A61K 9/51*** | (2006.01) |

(Continued)

(52) U.S. Cl.

CPC ............. *A61K 31/662* (2013.01); *A61K 9/1274* (2013.01); *A61K 9/5123* (2013.01); *A61K 31/05* (2013.01); *A61K 31/085* (2013.01); *A61K 31/137* (2013.01); *A61K 31/573* (2013.01); *A61K 31/685* (2013.01); *A61K 31/70* (2013.01); *A61K 45/06* (2013.01)

(58) Field of Classification Search

None

See application file for complete search history.

(56) References Cited

U.S. PATENT DOCUMENTS

| | | | | |
|---|---|---|---|---|
| 5,891,844 A * | 4/1999 | Hafner | ........................... | 514/1.5 |
| 6,180,142 B1 | 1/2001 | Taeusch | | |

(Continued)

FOREIGN PATENT DOCUMENTS

| | | | |
|---|---|---|---|
| IN | 241271 | | 6/2010 |
| IN | 241272 | | 6/2010 |
| IN | 241271 | * | 9/2013 |

OTHER PUBLICATIONS

Banerjee (Banerjee, R., Comparison of in vitro Surface Properties of Clove Oil-Phospholipid Suspensions with those of ALEC, Exosurf and Survanta, Pulm. Pharmacol. Ther., 14 (2001), pp. 85-91).*

(Continued)

*Primary Examiner* — Bethany Barham
*Assistant Examiner* — Dominic Lazaro
(74) *Attorney, Agent, or Firm* — Vorys, Sater, Seymour and Pease LLP

(57) ABSTRACT

A protein free surfactant composition comprising dipalmitoylphosphatidyl choline (DPPC) and eugenol having a ratio in the range of 10:5 to 4:2 with >99% airway patency in the presence of albumin, for treating acid lung injury, adult respiratory distress syndrome and meconium aspiration syndrome.

23 Claims, 21 Drawing Sheets

(51) Int. Cl.

| | |
|---|---|
| ***A61K 31/05*** | (2006.01) |
| ***A61K 31/137*** | (2006.01) |
| ***A61K 31/573*** | (2006.01) |
| ***A61K 31/685*** | (2006.01) |
| ***A61K 31/70*** | (2006.01) |

(56) References Cited

U.S. PATENT DOCUMENTS

| | | | | |
|---|---|---|---|---|
| 6,660,833 | B1 | 12/2003 | Walther et al. | |
| 6,887,845 | B2 | 5/2005 | Barron et al. | |
| 2005/0043227 | A1 * | 2/2005 | Compernolle | G01N 33/74 515/1.5 |

OTHER PUBLICATIONS

PCT International Search Report dated Feb. 23, 2012 for co-pending International Patent Application No. PCT/IN2011/000691.

PCT Written Opinion dated Feb. 23, 2012 for co-pending International Patent Application No. PCT/IN2011/000691.

Akrachalanont, P. "Preparation and Evaluation of Liposome Containing Clove Oil," *Thesis at Silpakorn University,* 2008, http://www.thapra.lib.su.ac.th/objects/thesis/fulltext/snamcn/Pilaslak__Akrachalanont/Fulltext.pdf, XP002669247.

Anonymous. "A Nanoparticle Exogenous Protein Free Micronutrient Added Pulmonary Surfactant Composition for Neonatal Respiratory Distress Syndrome (NRDS) and a Process for Preparing the Same," *Indian Institute of Technology Bombay Industrial Research & Consultancy Centre,* 2010, http://www.ircc.iitb.ac.in/IRCC-Webpage/patent1222, XP002669246.

Anzueto, A.; Baughman, R.; Guntupalli, K.; De Maria, E.; Davis, K.; Weg, J.; et al. "An International Randomized Placebo-Controlled Trial Evaluating the Safety and Efficacy of Aerosolized Surfactant in Patients with Sepsis-Induced ARDS," *AM. J. Respir. Crit. Care Med.,* 1994, 149, A567.

Anzueto, A.; Baughman, R.; Guntupalli, K.K.; Weg, J.G.; Wiedemann, H.P.; Raventos, A.A.; Lemaire, F.; Long, W.; Zaccardelli, D.S.; Pattishell, E.N. "Aerosolized Surfactant in Adults with Sepsis-Induced Acute Respiratory Distress Syndrome," *N. Eng. J. Med.,* 1996, 334, 1417-1421.

Banerjee, R.; et al. "Comparison of In Vitro Surface Properties of Clove Oil-Phospholipid Suspensions With Those of Alec, Exosurf and Survanta," *Pulmonary Pharmacology and Therapeutics,* 2001, 14, 85-91.

Banerjee, R.; et al. "In Vitro Evaluation of Surfactants With Eucalyptus Oil for Respiratory Distress Syndrome," *Respiration Physiology,* 2001, 126, 141-151, XP027253928.

Larsson, M.; Nylander, T.; Keough, K.M.W.; Nag, K. "An X-Ray Diffraction Study of Alterations in Bovine Lung Surfactant Bilayer Structures Induced by Albumin," *Chem. Phys. Lipids,* 2006, 144, 137-145.

Spragg, R.G.; Lewis, J.F.; Walmrath, H.D.; Johannigman, J.; Bellingan G.; Laterre, P.F.; et al. "Effect of Recombinant Surfactant Protein C Based Surfactant on the Acute Respiratory Distress Syndrome," *N. Eng. J. Med.,* 2004, 351, 884-892.

Taeusch, H.; de la Sena, J.; Perez-Gil, J.; Alonso, C.; Zasadzinski, J. "Inactivation of Pulmonary Surfactant Due to Serum-Inhibited Adsorption and Reversal by Hydrophilic Polymers: Experimental," *Biophys. J.,* 2005, 89, 1769-1779.

Graehl, Experiment 4: Steam Distillation of a Volatile Oil from Cloves, URL : <http://www.graehl.com/chem%20312/Experiment%204%20Steam%20Distillation%20of%20a%20Volatile% 20Oil% 20from%20Cloves.pdf >, retrieved from the Internet Dec. 30, 2015.

Oil of Clove, Wikipedia, URL: <https://en.wikipedia.org/wiki/Oil__of_clove>; retrieved from the Internet Dec. 30, 2015.

Eugenol, Wikipedia, URL : <https://en.wikipedia.org/wiki/Eugenol > retrieved from the Internet Dec. 30, 2015.

Eugenol, ChemSpider, Royal Society of Chemistry, URL : < http://www.chemspider.com/Chemical-Structure.13876103.html>, retrieved from the Internet Jan. 7, 2015.

Mastute Bello et al, An Official American Thorasic Society Workshop Report: Features and Measurements of Experimental Acute Lung Injury in Animals, Am J. Respir Cell Mol Biol, vol. 44, pp. 725-738, 2011.

Frank R. Giuliani, The Composition, Structure, Sources, and Applications of Eugenol, ESSAI, vol. 12, Article 19, Spring 2015.

* cited by examiner

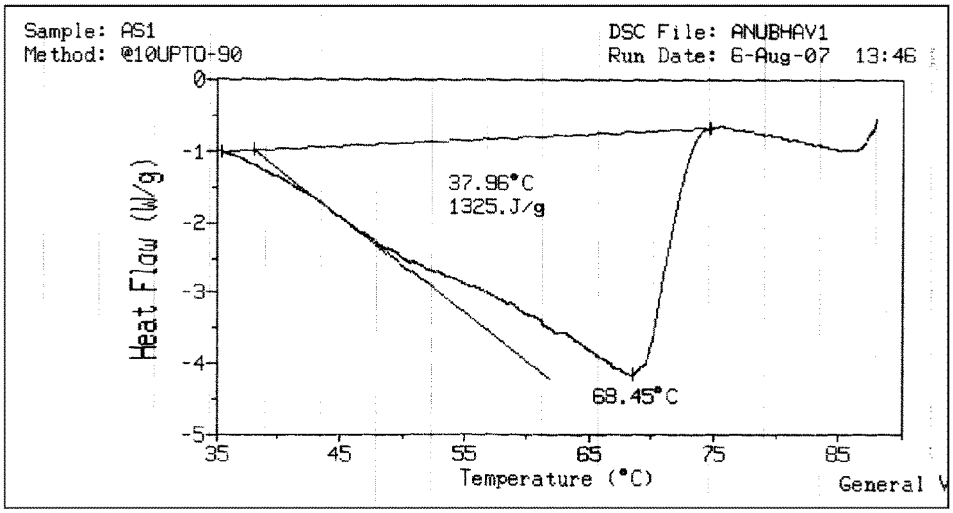
Figure 15. Thermogram of DPPC liposomes (1mg/ml)
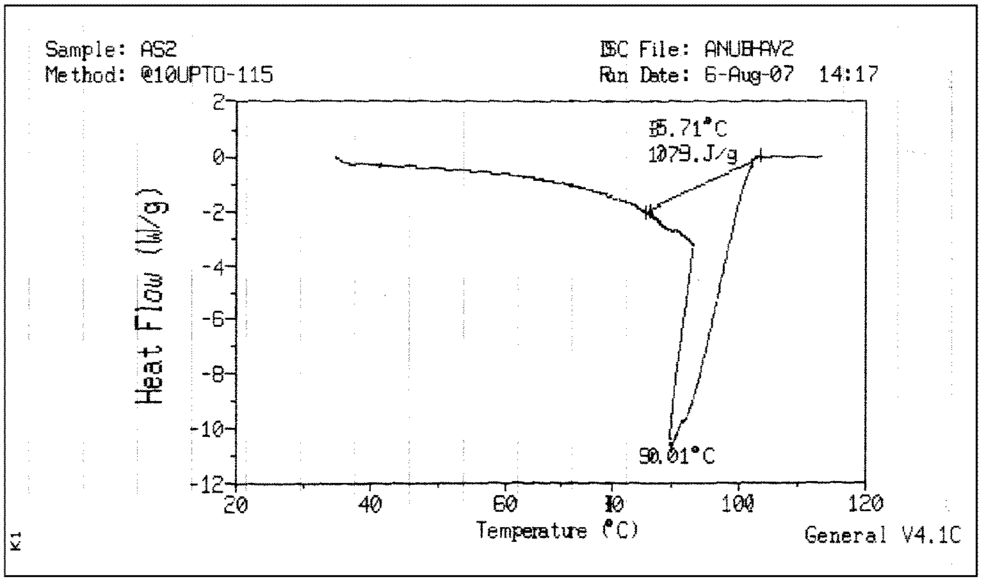
Figure 16. Thermogram of DPPC liposomes (1mg/ml) and Eugenol D1 sonicated (Combined)

Effective Diameter: 226.4 nm
Polydispersity: 0.172
Avg. Count Rate: 442.9 kcps
Baseline Index: 0.0
Elapsed Time: 00:01:20

| Run | Eff. Diam. (nm) | Half Width (nm) | Polydispersity | Baseline Index |
|---|---|---|---|---|
| 1 | 35482.1 | 31228.7 | 2.304 | 0.0 |
| 2 | 131.1 | 106.2 | 0.303 | 0.0 |
| 3 | 286.5 | 110.4 | 0.288 | 0.0 |
| 4 | 191.2 | 97.5 | 0.260 | 4.9 |
| 5 | 214.3 | 101.0 | 0.224 | 0.0 |
| Mean | 200.8 | 104.0 | 0.270 | 1.2 |
| Std. Error | 5.9 | 2.8 | 0.019 | 1.2 |
| Combined | 226.4 | 93.8 | 0.172 | 0.0 |

PROTEIN FREE SURFACTANT COMPOSITION FOR PULMONARY DISEASES AND A PROCESS FOR PREPARING THE SAME

CROSS REFERENCE TO RELATEDAPPLICATIONS

This application is the U.S. National Phase under 35 U.S.C. §371 of International Application No. PCT/IN11/00691, filed Oct. 4, 2011, designating the United States and published in English on Jun. 14, 2012, as WO 2012/077127, which claims priority to Indian Patent Application No. 3370/MUM/2010, filed Dec. 10, 2010, which is incorporated by reference in its entirety.

FIELD OF INVENTION

The present invention relates to a novel protein-free surfactant for Adult Respiratory Distress Syndrome (ARDS), Acute Lung Injury (ALI), Neonatal Respiratory Distress Syndrome (NRDS) and Meconium Aspiration Syndrome (MCS).

BACKGROUND OF THE INVENTION

At present Respiratory Distress Syndrome (RDS) affects around 1 in 6,800 people with Neonatal Respiratory Distress Syndrome (NRDS) occurring in 40,000 infants and Adult Respiratory Distress Syndrome (ARDS) in 150,000 adults in USA. The incidence of ARDS in developing countries like India is much higher around 20 per 1000 admissions in the intensive care unit. Meconium Aspiration Syndrome (MAS) affects 1-2% of all deliveries.

Lung surfactant is synthesized by alveolar type II cells and is a complex mixture of lipids (90%) and proteins (10%). The primary function of the lung surfactant is to lower the surface tension at the air-liquid interface, thus preventing alveolar collapse during end expiration and reducing the work of breathing. Rapid adsorption of pulmonary surfactant to the air-liquid interface is essential for normal breathing.

In inflammatory diseases and conditions of surfactant dysfunction like ARDS and acute lung injury, the alveoli are filled with a proteinaceous fluid rich in albumin and a large number of acute inflammatory cells. These agents inhibit the function of the endogenous surfactant. Samples of bronchoalveolar lavage fluid from ARDS patients have lower levels of dipalmitoylphosphatidylcholine (DPPC), phosphatidylglycerol and surfactant proteins as compared to healthy persons. Thus there appears to be a logical role of surfactant therapy in ARDS and acute lung injury including that due to acid aspiration. However, the results of large controlled clinical trials using presently available exogenous surfactants in ARDS have failed.

Pulmonary inflammation represents an important component in the development of lung injury and ARDS. Oxidative stress also contributes to surfactant dysfunction. Also, it is increasingly recognized that in ARDS, surfactants are dysfunctional due to their unfavorable interactions with albumin and other inhibitory agents like acids and research must be directed towards developing tailor made surfactants that overcome albumin inhibition. As alveoli are flooded with plasma proteins over the early stages of ARDS, endogenous, surfactant may be inactivated. Albumin and serum are known to inhibit surfactant function in acute lung injury by competitive adsorption and by decreased airway patency. Taeusch et al. have shown the detrimental effect of serum on the adsorption of lung surfactants (cf H. Taeusch, J. de la Sena, J. Perez-Gil, C. Alonso, J. Zasadzinski, Inactivation of pulmonary surfactant due to serum-inhibited adsorption and reversal by hydrophilic polymers: experimental., Biophys. J. 89 (2005) 1769-1779). A direct thinning of surfactant bilayers due to addition of 5 wt % albumin to bovine lung extract surfactant was observed by X Ray diffraction studies by Larsson et al. (cf. Larsson M, Nylander T, Keough K M W, Nag K. An X-Ray diffraction study of alterations in bovine lung surfactant bilayer structures induced by albumin. Chem. Phys. Lipids 2006; 144:137-145). Thus, there is a need to develop surfactants that have specific interactions with albumin that allow them to maintain high airway patency in the presence of albumin.

All clinical trials using surfactants designed for NRDS have failed in ARDS. One of the trials used aerosolised Exosurf, a synthetic surfactant that does not contain any surfactant-associated proteins, to patients with sepsis-induced ARDS for upto 5 days [cf Anzueto A, Baughman R, Guntupalli K, De Maria E, Davis K, Weg J et al. "An international randomized placebo-controlled trial evaluating the safety and efficacy of aerosolized surfactant in patients with sepsis-induced ARDS". AM. J. Respir. Crit. Care Med. 1994; 149: A567 and Anzueto A, Baughman R P, Guntupalli K K, Weg J G, Wiedemann H P, Raventos A A, Lemaire F, Long W, Zaccardelli D S, Pattishell E N "Aerosolized surfactant in adults with sepsis-induced acute respiratory distress syndrome" N. Eng. J. Med. 1996; 334:1417-21).

No differences in oxygenation, ventilator-free days or mortality were observed between the surfactant-treated and placebo groups. Other trials using lusupultide (containing lipids and recombinant SP-C) when administered in doses of 50 mg PL/kg up to 4 times over 24 hours, to patients with ARDS due to a variety of aetiologies, did not show any difference in the ventilator free days or overall survival [cf Spragg R G, Lewis J F, Walmrath H D, Johannigman J, Bellingan G Laterre P F et al. Effect of recombinant surfactant protein C based surfactant on the acute respiratory distress syndrome. N. Eng. J. Med. 2004; 351 (9):884-892).

However, at present there are no effective surfactants available for therapy in ARDS and Acute Lung Injury (ALI). The present invention addresses these shortcomings as it can overcome the inhibition caused by albumin using a unique protein-free surfactant that forms non-lamellar phases Further, meconium aspiration syndrome is a condition where there is a secondary inactivation of the surfactant due to the presence of meconium. There is a need to develop surfactants that can prevent the meconium induced inhibition and maintain airway patency in the presence of meconium.

PRIOR ART

U.S. Pat. No. 6,887,845 teaches the development of polypeptoid pulmonary surfactants. The invention provides spreading agents based on sequence-specific oligomers comprising a peptoid, a peptide-peptoid chimera, a retropeptoid or a retro(peptoid-peptide) chimera, and methods for using the same, including for the treatment of respiratory distress of the lungs. The spreading agents are sequence-specific oligomers, including retrosequence-specific oligomers, based on a peptide backbone, that are designed as analogs of surfactant protein-B or surfactant protein-C. This involves the development of protein based analogs of high cost and does not address their ability to overcome inhibition in acute lung injury and meconium aspiration syndrome.

U.S. Pat. No. 660,833 deals with technologies for Respiratory Distress Syndrome (RDS) therapy with peptide analogs of human SP-B. A therapeutic pharmaceutical composition for the treatment of respiratory disease is disclosed, including particularly RDS. The composition is comprised of a synthetic dimer of an N-terminal fragment of Surfactant Protein B (SP-B) that advantageously mimics the functional activity of native human Surfactant Protein B, and to therapeutic methods of administration of such pharmaceutical compositions. This involves the development of protein based dimers of high cost and does not address their ability to overcome inhibition in acute lung injury and meconium aspiration syndrome:

U.S. Pat. No. 6,180,142 describes the reduction of surfactant inactivation in pulmonary surfactant therapy. Nonionic hydrophilic polymers or carbohydrates are administered either individually or in conjunction with therapeutically active pulmonary surfactants for the treatment of a variety of lung ailments. Included among the activities of these agents is their ability to reduce the inactivation of the surfactants by endogenous substances present in the lung. The invention deals with high molecular weight polymers that can cause disturbances in the osmotic balance in the lungs and may induce adverse inflammatory reactions.

Indian Patent 241272 of the Applicant describes an exogenous protein-free pulmonary surfactant composition for treating Adult Respiratory Syndrome (ARDS) comprising in a ratio of 2:1 or 1:1 w/v of dipalmitoyl phosphatidylcholine to eucalyptus oil in a normal saline medium (calcium free). The composition is in the form of nanoparticles of 500-800 nm. The surface tension of composition on film compression in the presence if erythrocytic membranes and inhibitory agents is 0-3 mN/m. The process for producing the protein-free pulmonary surfactant composition for treating adult respiratory syndrome comprised the steps of: preparing a solution of dipalmitoylphosphatidylcholine in an organic solvent, drying the same under vacuum at 40 C, adding calcium free aqueous isotonic electrolyte solution and eucalyptus oil in a ratio of 2 parts of dipalmitoylphosphatidylcholine to 1 part of oil or 1 part of dipalmitoylphosphatidylcholine to 1 part of oil and hydrating the mixture in a rotary vacuum evaporator for a period of 1 hour at 37 C. Prior to hydration, the pH of the solution was adjusted to 7.2 to 7.4. This patent does not deal with the ability of surfactants to overcome airway patency due to albumin, meconium and acids and does not deal with eugenol added surfactants.

Indian Patent 241271 of the Applicant describes a nanoparticulate exogenous protein-free pulmonary surfactant composition for treating Neonatal Respiratory Distress Syndrome comprising dipalmitoylphosphatidylcholine and clove oil or eucalyptus oil and ascorbic acid in the ratio of 10:3:0.1 w/v/w with or without calcium salts and consisting of particle sizes 150-450 in diameter. The composition contains ascorbic acid at 0.1 mg/ml. The surface tension of composition on film compression is 0-4.5mN/m. The composition contains dipalmitoylphosphatidylcholine to clove oil or dipalmitoylphosphatidylcholine to eucalyptus oil in a ratio of 10:3 w/v. The process for producing the nanoparticulate exogenous protein-free pulmonary surfactant composition for treating Neonatal Respiratory Distress Syndrome comprised the steps of:—preparing a solution of dipalmitoylphosphatidylcholine in an organic solvent, drying the same under vacuum at 40° C., adding aqueous isotonic electrolyte solution, ascorbic acid and either of clove oil or eucalyptus oil thereto, in a ratio of 10 parts of dipalmitoylphosphatidylcholine to 3 parts of oil to 0.1 parts of ascorbic acid and hydrating the mixture in a rotary vacuum evaporator for a period of 1 hour at 37° C. The pH of the solution is adjusted to 7.2 to 7.4 prior to hydration. This patent does not deal with the ability of the surfactants to overcome inhibition due to albumin, meconium and acids and improve airway patency. Though eugenol is a constituent of clove oil, but not of eucalyptus oil, it is surprisingly found that eugenol has some benefits due to synergistic effects when used in a specific ratio with dipalmitoylphosphatidylcholine which are unique and unexpected and not seen with clove oil or eucalyptus oil.

OBJECT OF INVENTION

The object of the invention is to provide a protein-free surfactant that is free from variability, and prevents adverse interactions with albumin, acids and meconium for therapy in Acute Lung Injury, Adult Respiratory Distress Syndrome, Meconium Aspiration Syndrome, Neonatal Respiratory Distress Syndrome and other inflammatory lung diseases.

BRIEF DESCRIPTION OF INVENTION

The invention deals with the formulation of a synthetic surfactant for curing Acute Respiratory Distress Syndrome, Acid Lung Injury and Meconium Aspiration Syndrome wherein the lungs fail to function, due to abnormal functions of Pulmonary Surfactants which are inhibited by the agents like albumin, acids, serum, meconium that flood the alveoli. The same formulation may be used for curing other disorders such as Neonatal Respiratory Disease (NRDS), acid induced lung injury, Meconium Aspiration Syndrome (MAS) etc.

Natural pulmonary surfactant is made up of several lipids and proteins, wherein dipalmitoylphosphatidylcholine (DPPC) forms the major lipid composition along with several other unsaturated phospholipids like phosphatidylglycerol, palmitoyloleoyl phosphatidylcholine etc. DPPC alone is not effective as a surfactant.

The present invention is a formulation comprising only DPPC and Eugenol in a ratio of 5:3 which act synergistically to overcome the adsorption barriers due to inhibitors like albumin and acids, to form non-lamellar phases with superior surface activity, to form nanosized domains in the presence of albumin and to maintain 100% airway patency in presence of albumin. Eugenol is a primary derivative of clove oil but not of eucalyptus oil. However, clove oil has many other constituents which hamper its ability to maintain airway patency. Clove oil is only known to be useful in NRDS due to its ability to lower the surface tension but does not form non-lamellar phases, nor forms nanodomains with albumin nor achieves high airway patency in presence of albumin. The formulation has a unique ability to form non-lamellar phases, form nanodomains in the presence of albumin, and to improve the adsorption rate and airway patency in the presence of albumin, acids, serum and meconium. These unique features allow it to overcome inhibition by albumin, serum, acids, meconium and to mimic the functions of natural surfactants containing surfactant specific proteins.

The invented surfactant consists of DPPC: eugenol 5:3 in a saline medium containing calcium and is referred to as Nanosurf or invented surfactant. Curosurf is a commercially available animal derived surfactant. Meconium is the first passed stool of the newborn which is aspirated in Meconium Aspiration Syndrome.

The advantages and/or unique features of the present invention are summarized as follows:

- Simple formulation of dipalmitoylphosphatidylcholine and eugenol in a ratio of 5:3 which act synergistically and form non-lamellar phases in the presence of inhibitors
- High airway patency in the presence of albumin due to its specific interactions with albumin

- Overcomes adsorption barriers due to albumin
- Formation of nanosized domains of 75 nm with surface roughness of 9 nm in the presence of albumin
- High airway patency in the presence of meconium
- High airway patency of broncholaveolar lavage fluid when given to acid injured lungs
- Reduction of TNF alpha when given to acid injured lungs
- No requirement of ascorbic acid, the presence of which adversely affects the interactions with albumin
- No requirement of complex multicomponent herbal oils which may have variability in composition
- Spontaneous formation of nanovesicles and networked tubes by a simple process

BRIEF DESCRIPTION OF FIGURES

FIG. 15 is a Thermogram of DPPC liposomes (1 mg/ml)

FIG. 16 is a Thermogram of DPPC liposomes (1 mg/ml) and Eugenol

DETAILED DESCRIPTION OF INVENTION

The invented formulation is a protein-free synthetic surfactant useful for the treatment of surfactant dysfunctional conditions and related inflammatory conditions like ARDS, acute lung injury, meconium aspiration syndrome.

The invented formulation consists of at least one phospholipid particularly dipalmitoylphosphatidyl choline (DPPC) and eugenol having a ratio in the range of 10:5 to 4:2 by weight and is free of ascorbic acid.

In another embodiment of the invention, the invented formulation consists of at least one phospholipid particularly dipalmitoylphosphatidyl choline (DPPC) and eugenol having a ratio of 5:3 by weight and is free of ascorbic acid.

The invented formulation is made by forming liposomes using thin film hydration method. A desired amount of lipid (DPPC) is dissolved with 2:1 chloroform: methanol mixture and a thin film of lipid is made using rotary vacuum evaporator at 40° C. in order to completely remove the organic solvent mixture. The thin lipid film is then hydrated with hydrating medium composed of 0.9% sodium chloride and 2 mM calcium chloride at pH 7.4. The hydration is carried out for 1 hour at 45° C. After hydration, eugenol is added to the liposomes and carefully mixed.

Figure 4:
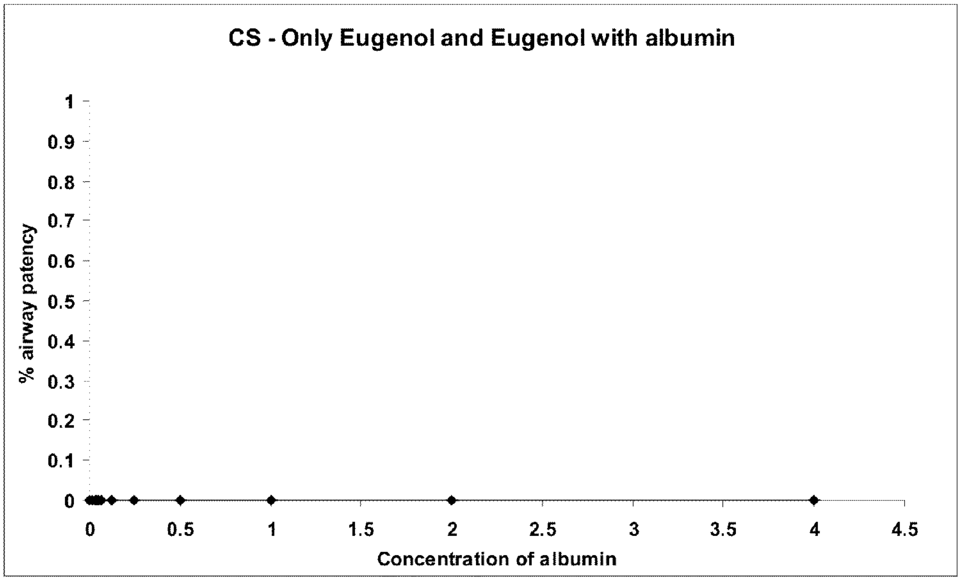
FIG. 4 shows airway patency due to eugenol in the presence of graded amounts of albumin
Figure 5:
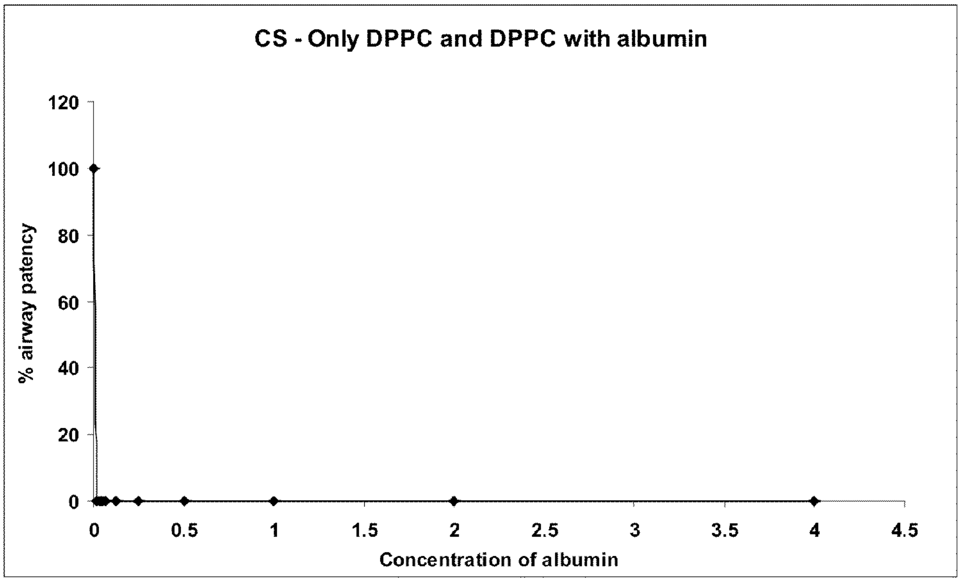
FIG. 5 shows airway patency of DPPC alone in the presence of graded amounts of albumin
Figure 6:
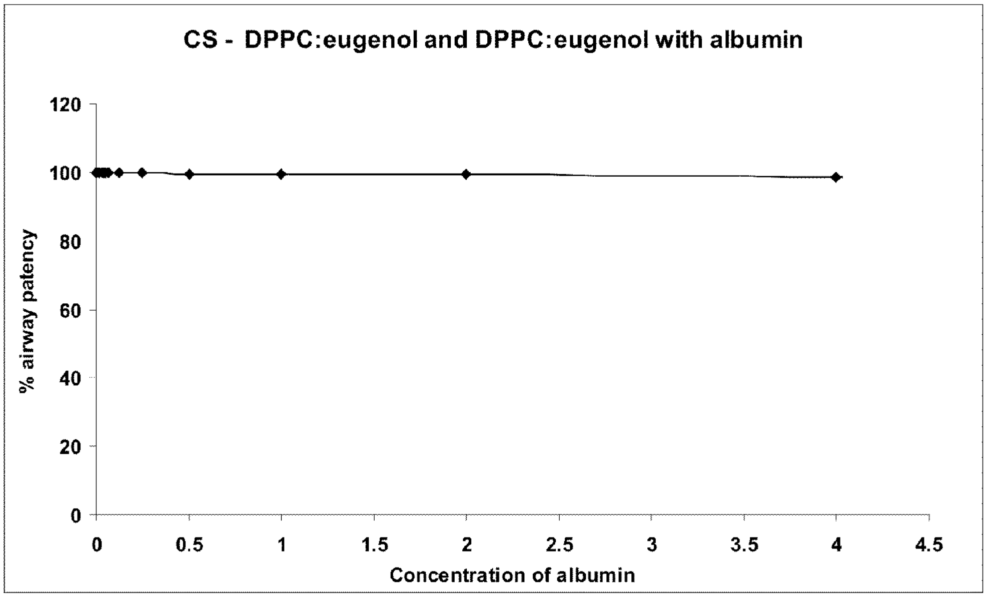
FIG. 6 shows airway patency of DPPC: eugenol in the presence of graded amounts of albumin

The features of the surfactant are due to synergistic effects of DPPC and eugenol which lead to the formation of non-lamellar phases and maintains 100% airway patency in the presence of albumin. FIGS. 4, 5 and 6 show that DPPC alone shows 0% patency in presence of albumin and eugenol alone shows 0% airway patency in the presence of albumin but surprisingly the DPPC: eugenol combination in a ratio of 5:3 shows 100% airway patency in presence of albumin.

Figure 1:
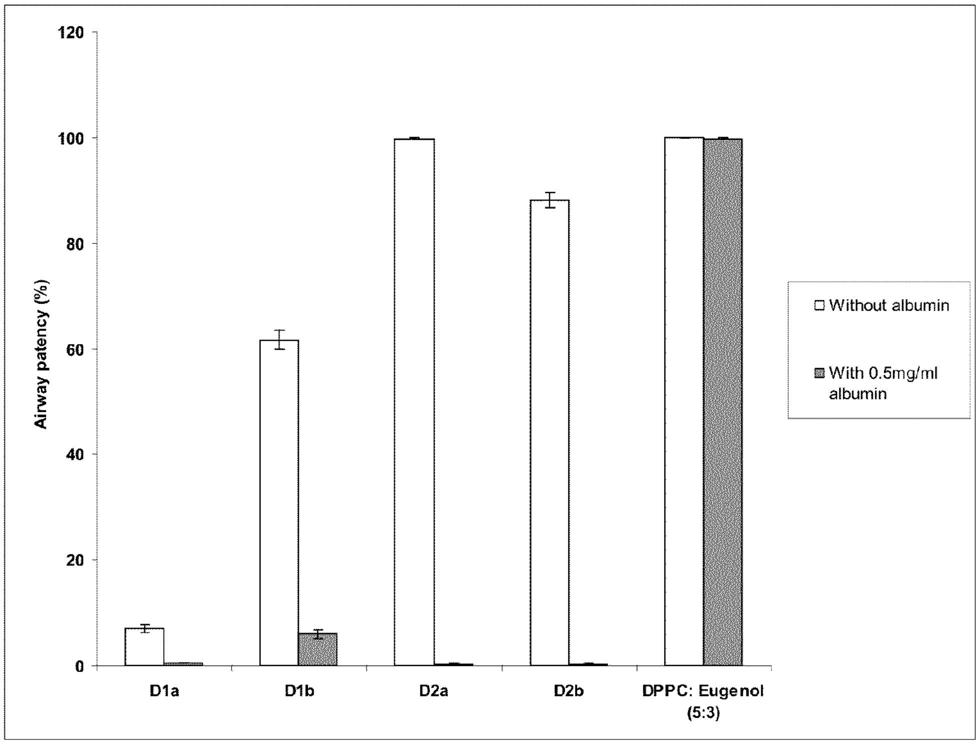
FIG. 1 shows comparison of airway patency due to the prior patent formulations and present invention in the presence of albumin

FIG. 1 depicts the superiority of the present invention vis-à-vis the formulations claimed in Indian Patent 241271 and Indian Patent 241272. Wherein D1a and D1b refers to compositions claimed in Indian patent 241271 whereas D2a and D2b refer to compositions claimed in Indian patent 241272. D1a consists of DPPC+clove oil+ascorbic acid in the ratio 10:3:0.1 prepared in accordance with 241271. D1b consists of DPPC+eucalyptus oil+ascorbic acid in the ratio 10:3:0.1 prepared in accordance with 241271.

D2a consists of DPPC +eucalyptus oil in a 2:1 ratio in normal saline prepared in accordance with 241272. D2b consists of DPPC+eucalyptus oil in a 1:1 ratio in normal saline prepared in accordance with 241272. DPPC: eugenol 5:3 denotes the present invention.

The white bars depict the airway patency of the formulations whereas the grey bars depict the airway patency in the presence of albumin. It is clearly seen that D1a has 0.4% airway opening in presence of albumin, D1b has 6% airway opening in presence of albumin, D2a has 0.3% airway opening in presence of albumin, D2b has 0.2% airway opening in presence of albumin whereas the present invention has 99.8% airway opening in presence of albumin.

TABLE 1

The actual values of airway patency plotted in FIG. 1

| | Airway patency (%) | std dev |
|---|---|---|
| D1a | 6.97 | 0.78 |
| D1a in presence of 0.5 mg/ml albumin | 0.4 | 0 |
| D1b | 61.63 | 1.86 |
| D1b in presence of 0.5 mg/ml albumin | 6.03 | 0.85 |
| D2a | 99.83 | 0.06 |
| D2a in presence of 0.5 mg/ml albumin | 0.3 | 0.26 |
| D2b | 88.07 | 1.45 |
| D2b in presence of 0.5 mg/ml albumin | 0.23 | 0.25 |
| DPPC:Eugenol (5:3) | 99.9 | 0 |
| DPPC:Eugenol (5:3) + 0.5 mg/ml albumin | 99.83 | 0.06 |

Superiority of eugenol added surfactant as compared to clove oil added surfactant DPPC: eugenol act synergistically to prevent adverse interactions in the presence of albumin, leading to an increased airway patency. This feature is not fulfilled by DPPC:clove oil and is hampered by the presence of ascorbic acid.

Figure 2:
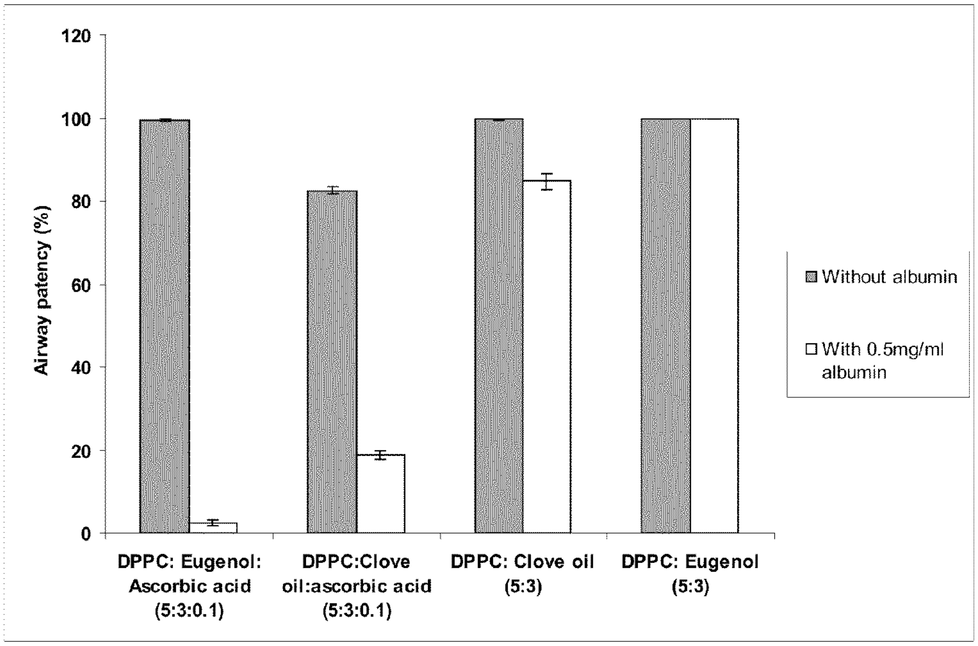
FIG. 2 shows airway patency of invented formulation and clove oil added surfactants

In FIG. 2 the airway patency of DPPC:Eugenol 5:3 (present invention) with that of DPPC:clove oil 5:3 in the absence and presence of albumin is compared. It is seen that the airway patency of DPPC:clove oil 5:3 in the presence of albumin is 84.7+/−1.8% whereas the airway patency of DPPC: eugenol 5:3 in the presence of albumin is 99.8+/−0.1%.

Further, it is noted that the presence of ascorbic acid is detrimental to the interaction with albumin. The airway patency of DPPC: eugenol :ascorbic acid 5:3:0.1 in the presence of albumin is 2.4+/−0.7% whereas the airway patency of DPPC: eugenol 5:3 in the presence of albumin is 99.8+/−0.1%. Similarly, DPPC:cloveoil:ascorbic acid 5:3:0.1 in the presence of albumin showed an airway patency of 18.8+/−0.9 whereas the airway patency of DPPC:clove oil 5:3 in the presence of albumin was 84.7+/−1.8% and of DPPC: eugenol 5:3 in the presence of albumin was 99.8+/−0.1%

Figure 3:
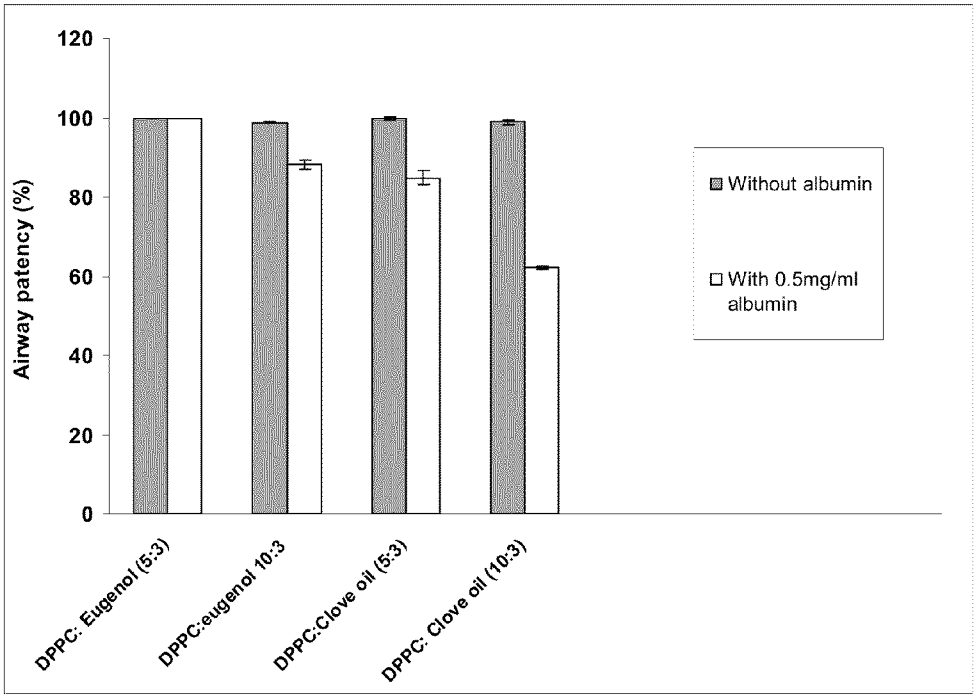
FIG. 3 shows airway patency of specific ratios of DPPC: eugenol surfactants

A unique combination of DPPC: eugenol 5:3 shows beneficial interactions in the presence of albumin which cause an increased airway patency in the presence of albumin. FIG. 3 depicts this effect. It is seen that the airway patency for DPPC: eugenol 5:3 in the presence of albumin is 99.8=/−0.1% whereas the airway patency of DPPC: eugenol 10:3 in the presence of albumin is 88.2+/−1.3%. Similarly, it is seen that DPPC:clove oil 5:3 in the presence of albumin is 84.8+/−1.8% whereas DPPC:clove oil 10:3 in the presence of albumin is 61.97+/−0.38% whereas the airway patency of DPPC: eugenol 5:3 in the presence of albumin is 99.8=/−0.1%.

FIG. 4 reflects airway patency due to eugenol in the presence of graded amounts of albumin and FIG. 5 shows airway patency of DPPC alone in the presence of graded amounts of albumin. FIG. 6 shows airway patency of DPPC: eugenol in the presence of graded amounts of albumin The invented formulation can be used as an inhalable surfactant in acute lung injury, ARDS, MAS, NRDS, and other inflammatory lung diseases. It can also be delivered as an intratracheal in for ARDS and NRDS. The invented surfactant can also be used to deliver drugs to the airways and alveoli.

Figure 7:
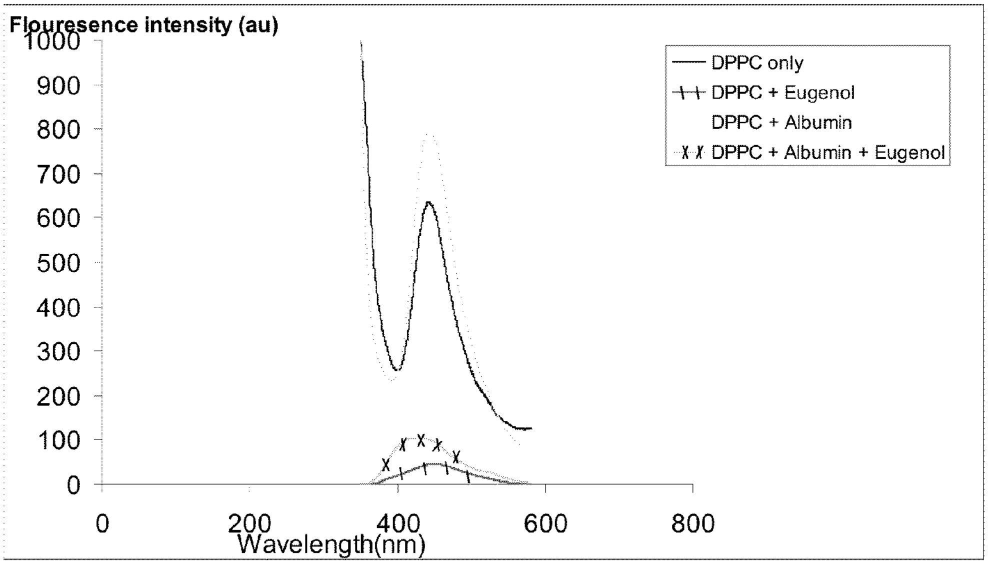
FIG. 7 shows Laurdan fluorescence of DPPC eugenol and DPPC alone in the presence and absence of albumin

Another embodiment of the invention is the formation of non-lamellar phases with improved surface activity in the presence of inhibitors. This is depicted by change in Laurdan fluorescence and presence of asymmetric $PO_2^-$ stretching vibration band in FTIR spectroscopy. FIG. 7 depicts the Laurdan fluorescence of the invented formulation depicting the formation of non-lamellar phases in the presence of albumin. From FIG. 7 and table 2, the ratio of Laurdan fluorescence in 360 and 390 nm shows that DPPC and DPPC in the presence of albumin give ratios of 2.6 and 1.98 respectively (>1). On the other hand, DPPC: eugenol and DPPC: eugenol in the presence of albumin give laurdan fluorescence in 360 and 390 nm of 0.006 and 0.56 respectively (<1). Similarly, on comparing the fluorescence in 360 and 490 nm, it is seen that DPPC alone and DPPC in the presence of albumin give ratios of 2.41 and 1.21 respectively (>1). On the other hand, DPPC: eugenol and DPPC: eugenol in the presence of albumin give Laurdan fluorescence in 360 & 490 nm of 0.003 and 0.077 respectively (<1). Laurdan (6-dodecanoyl-2-dimethylaminonaphthalene) is a fluorescent membrane probe that has the advantage of displaying spectral sensitivity to the phospholipids phase state. Laurdan is located at the hydrophilic-hydrophobic interface of the bilayer and shows sensitivity to the polarity of its environment. Hence, shifts in its spectra can be used to depict membrane perturbations and phase changes. In this case, DPPC: eugenol show a different spectral profile than that of DPPC alone and this is evident even in the presence of albumin.

TABLE 2

Ratio of Laurdan fluorescence at different wavelengths

| 360/390 | 360/490 | |
|---|---|---|
| 2.614831 | 2.409978 | DPPC |
| 0.005928 | 0.003196 | DPPC:eugenol |
| 1.989838 | 1.214862 | DPPC + albumin |
| 0.056589 | 0.077369 | DPPC:eugenol + albumin |

Figure 8:
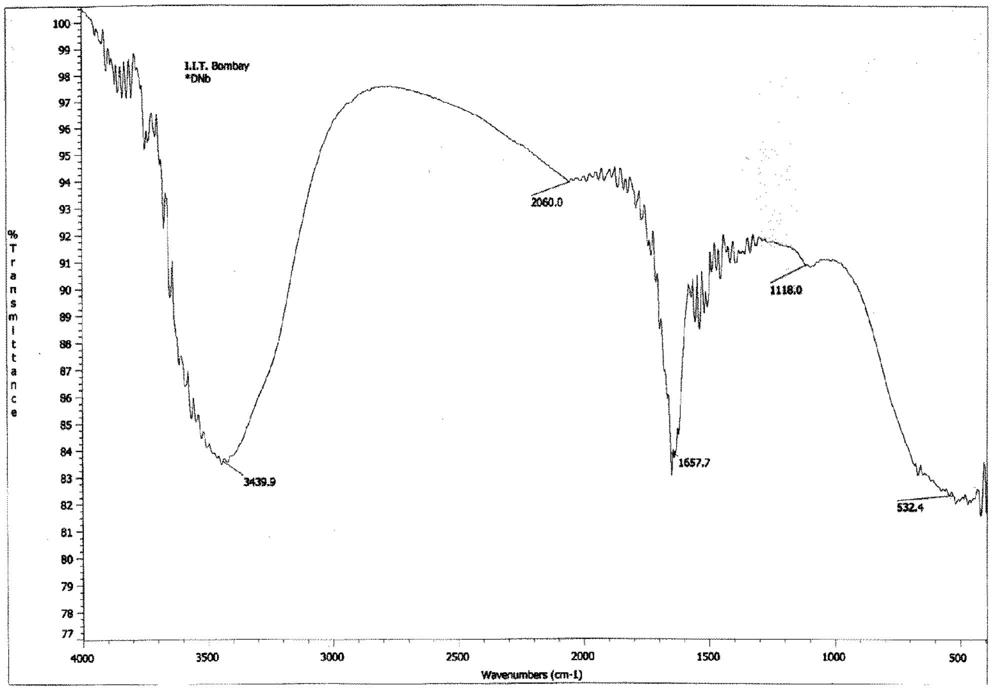
FIG. 8 shows DPPC in the presence of nitric acid
Figure 9:
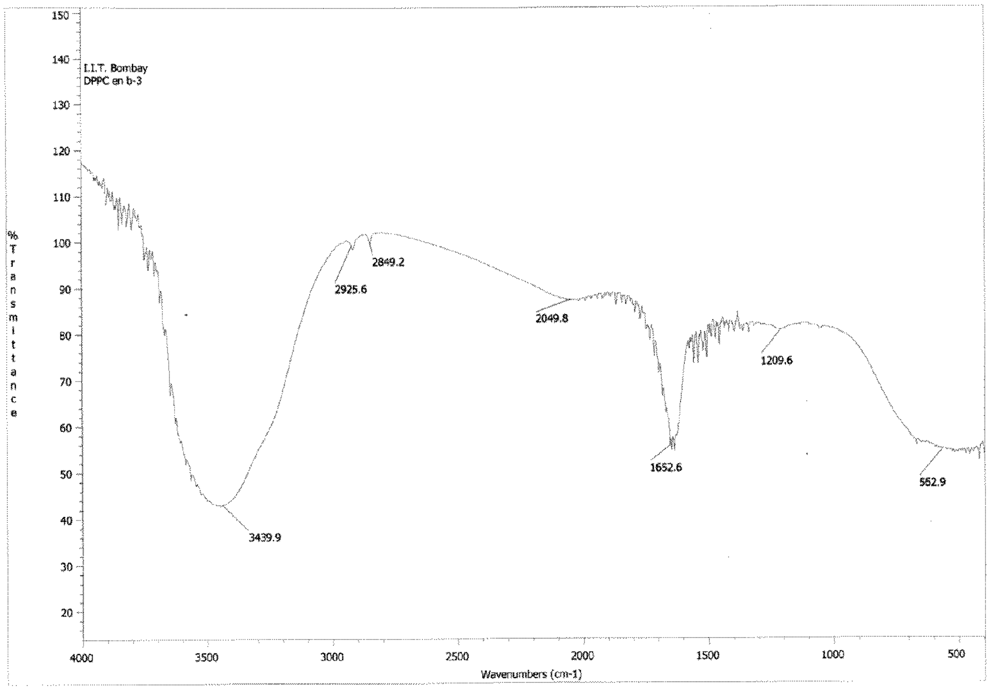
FIG. 9 shows DPPC: eugenol in the presence of nitric acid

FTIR spectroscopy has also shown the formation of non-lamellar phases by DPPC: eugenol in the presence of acid inhibitors. FTIR can give information about different parts of the molecule. The bands corresponding to C—H (symmetric) and C═O stretching vibrations are used to detect phase transitions. The phosphate group undergoes an important reorganization during lamellar to non-lamellar phase transition. The lamellar to non-lamellar phase transition can also be explained by change in the degree of water hydrogen bonding to the phosphate group. The shift in the wave number characteristic for the asymmetric $PO_2^-$ stretching vibration bands and $CH_2$ symmetric bands by eugenol was observed in the FTIR spectra. This suggests the lamellar to non-lamellar phase transition was observed in DPPC: eugenol even in presence of surfactant inhibitors. FIG. 8 represents FTIR of DPPC in the presence of nitric acid (as an inhibitor). FIG. 9 represents the FTIR of DPPC: eugenol in the presence of nitric acid.

DPPC and nitric acid: DPPC in the presence of acid gave broad peak ranging from 3439 $cm^{-1}$ to 3460.3 $cm^{-1}$ (indicative of aqueous water, O—H and C—C). Infrared bands characteristic of phosphate group in phospholipids occur in the region 1000-1300 $cm^{-1}$ (indicative of single bond P—O and double bond P═O stretching bands). A sharp peak at 1118 $cm^{-1}$ (characteristic of asymmetric $PO_2^-$ stretching vibration band) was obtained for DPPC liposomes in presence of nitric acid (pH 5). Strong peaks at 1118 $cm^{-1}$ (indicative of symmetric stretch of nitrate ion) for DPPC liposomes were obtained with nitric acid at pH 5 respectively (see FIG. 8)

DPPC:Eugenol in presence of nitric acid: This peak shifted to 1209.6 $cm^{-1}$ (characteristic of single bond P—O, double bond P═O stretching and asymmetric $PO_2^-$ stretching vibration bands) in presence of eugenol for DPPC liposomes with nitric acid (pH 5). This suggests that eugenol induced lamellar to non-lamellar phase transition of DPPC liposomes as a result of which the phosphate group showed a shift in the wavenumber. In presence of eugenol, DPPC liposomes treated with nitric acid (pH 5) showed sharp peaks at 1209.6 $cm^{-1}$ (for asymmetric $PO_2^-$ stretching vibration band) and 2849.2 $cm^{-1}$ (indicating symmetric CH2 band). These peaks were not observed in the absence of eugenol. This shift suggests the lamellar to non-lamellar phase transition of DPPC liposomes by eugenol. Presence of asymmetric $PO_2^-$ stretching vibration band indicates the lamellar—$H_H$—hexagonal phase transition. The lamellar to non-lamellar phase transition can also be explained by change in the degree of water hydrogen bonding to the phosphate group. (FIG. 9)

Figure 10:
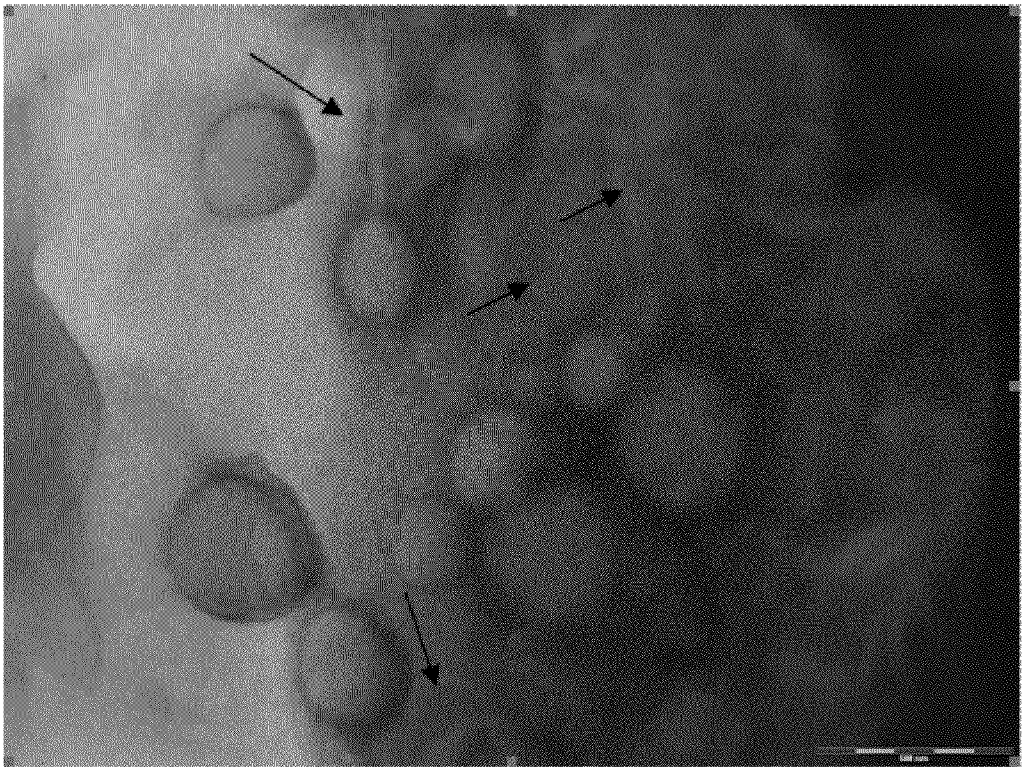
FIG. 10 shows TEM of DPPC: eugenol vesicles and networked tubes. Bar indicates 500 nm

Another embodiment of the invention is the formation of networked tubes as seen by TEM (FIG. 10). The invented formulation shows nanosized vesicles and networked tubes as seen in FIG. 10.

Figure 11:
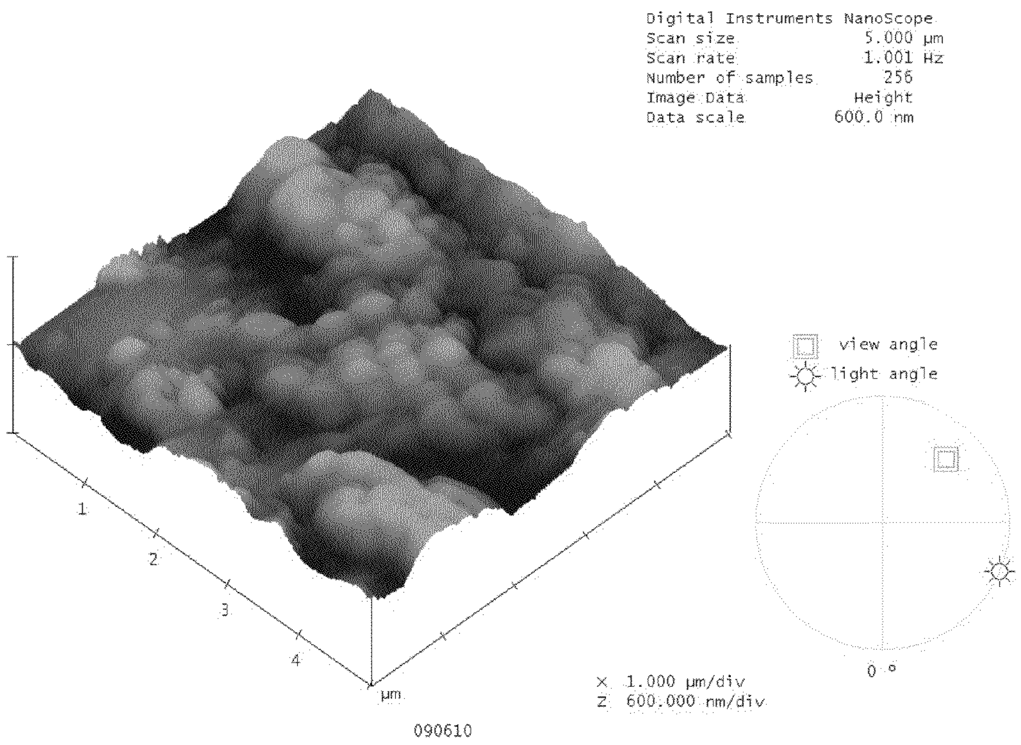
FIG. 11 shows AFM image of DPPC in the presence of albumin (3D topography)
Figure 12:
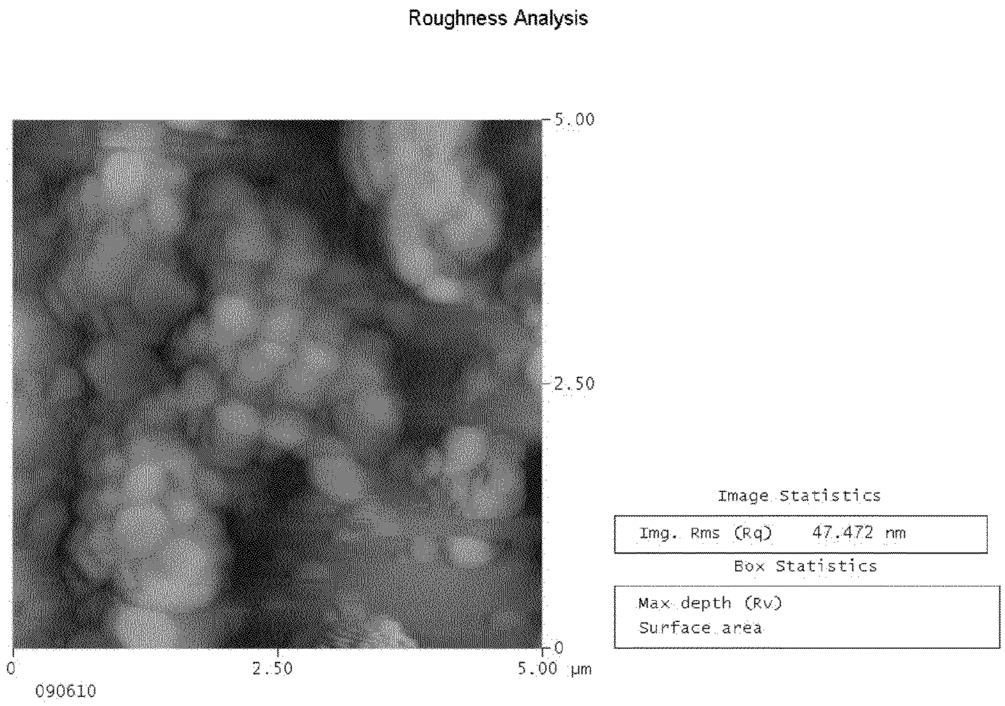
FIG. 12 shows surface roughness of DPPC in the presence of albumin
Figure 13:
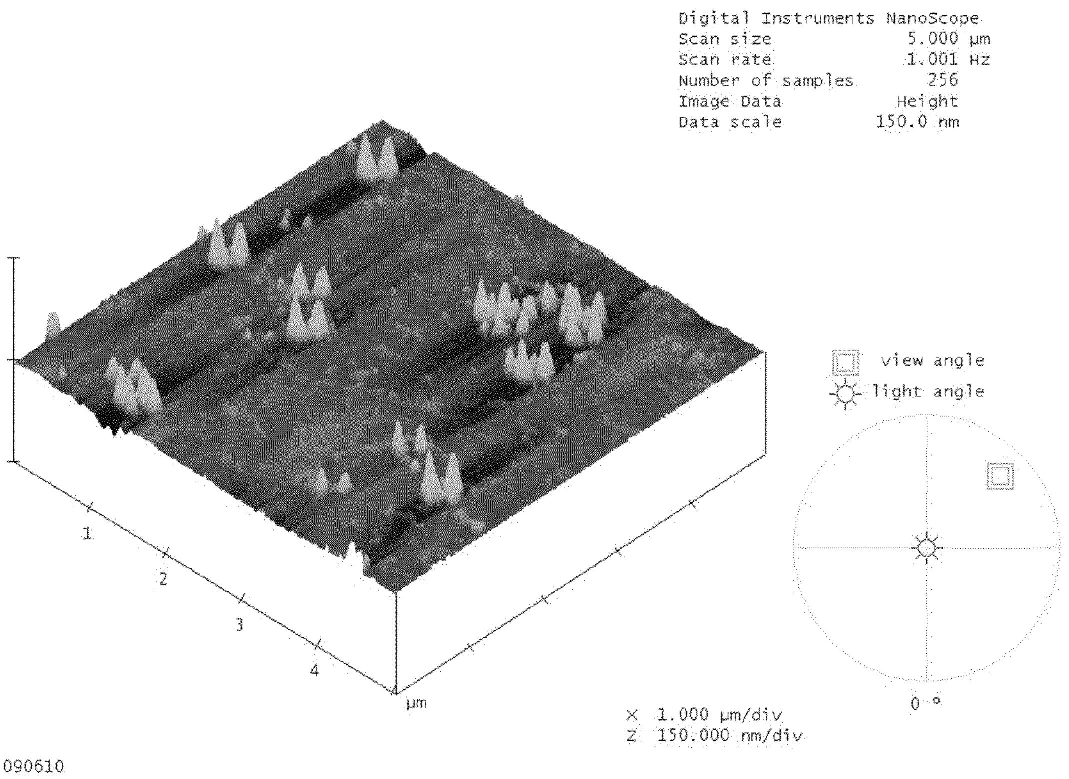
FIG. 13 shows AFM image of DPPC: eugenol in the presence of albumin (3D topography)
Figure 14:
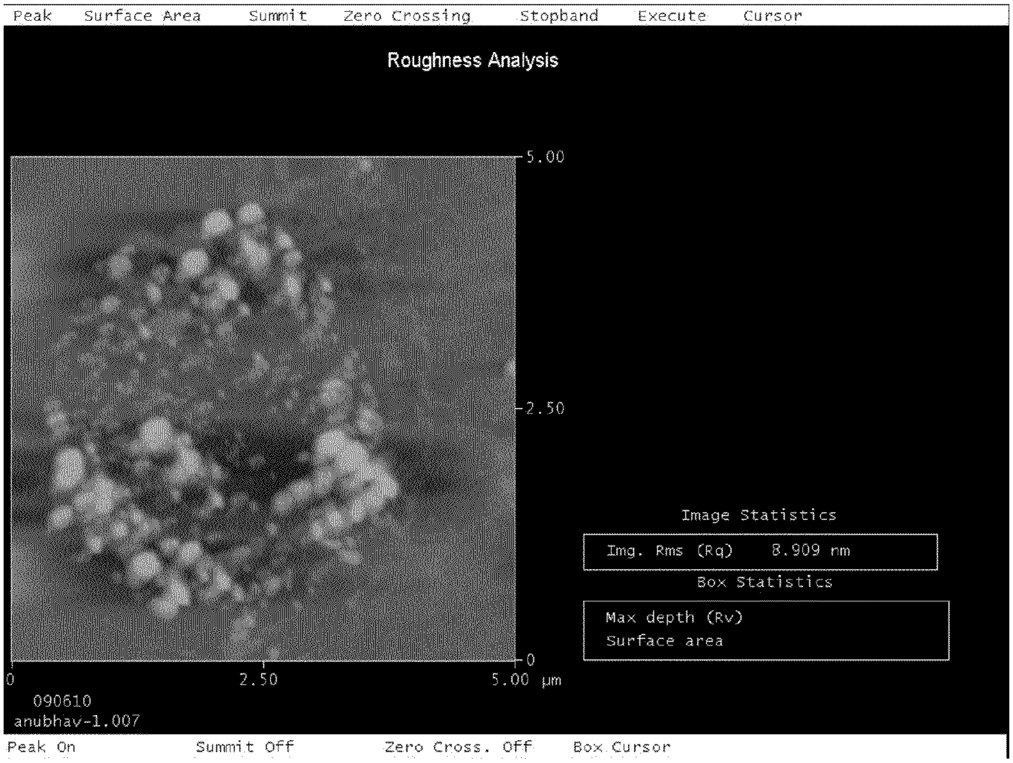
FIG. 14 shows surface roughness of DPPC: eugenol in the presence of albumin

AFM images of DPPC:albumin and DPPC: eugenol in the presence of albumin are depicted in FIGS. 11 and 13 respectively and the, roughness of the structures are depicted in FIGS. 12 and 14.

FIG. 11 of DPPC in the presence of albumin shows large aggregates of 540-550 nm sized domains whereas in FIG. 13 of DPPC: eugenol in the presence of albumin clearly defined closely packed domains of 80-90 nm.

The surface roughness of DPPC in the presence of albumin is depicted in FIG. 12. It confirms large aggregates with roughness of 47.47 nm. On the other hand, in the case of DPPC: eugenol in the presence of albumin, the surface roughness is only 8.9 nm as depicted in FIG. 14.

The formulation also causes a decrease in the activation energy for adsorption in the presence of acids as seen by comparing FIGS. 15, 16, 17 and 18. By lowering the energy barrier, the rate of adsorption of DPPC: eugenol is greatly enhanced.

Differential scanning calorimetry (DSC) was used to determine the mechanism of action of eugenol and DSC results proved that there was a change in the energy required by the liposomes to reach the interface for adsorption. The mechanism of action of Eugenol based on DSC results is that eugenol reduces the energy required by the liposomes to reach the interface and thereby enhances the rate of adsorption. The lower the energy required by the liposomes, better is the rate of adsorption. The liposomes from the bulk have to reach the interface for adsorption to take place. The energy barrier on the interface prevents the entry of liposomes, as a result, the liposomes fail to adsorb rapidly. For rapid adsorption to take place, the liposomes should be able to overcome the energy barrier which would enable them to reach the interface quickly Differential scanning calorimetry (DSC) was also used to study the interaction of bioactive compounds with model lipid bilayers such as DPPC. The experiments were performed at temperature ranging from 35° C. to 115° C. The rate of heating was 3° C./min and the system was allowed to cool to about 35° C. before the next experiment. The samples studied in the order of DSC results were, 1. DPPC liposomes (1 mg/ml) (see FIG. 15)

There was a large energy requirement (1325 J/g) of both acid-untreated and eugenol-untreated liposomes to reach the interface which slowed down the rate of adsorption (44.66±1.71 mN/m).

2. DPPC liposomes (1 mg/ml) and Eugenol (see FIG. 16)

There was an improved adsorption (31.49±0.43 mN/m) seen with these eugenol-treated liposomes as the energy (1079 J/g) required for the liposomes to reach the interface was much lower than the Eugenol-untreated and acid-untreated liposomes where the energy was 1325 J/g and the rate of adsorption was (44.66±1.71 mN/m).

3. DPPC liposomes (1 mg/ml) and HCl ($3.1\times10^{-1}$ moles/$dm^3$) (see FIG. 17)

On addition of HCl, there was an increase in the energy (1743 J/g) which probably affected the adsorption (59.89±2.22 mN/m) of these acid-treated liposomes. The energy barrier prevented the rapid entry of these liposomes at the interface thereby affecting adsorption.

4. DPPC liposomes (1 mg/ml) and HCl. ($3.1\times10^{-1}$ moles/$dm^3$) and Eugenol (see FIG. 18)

There was an improved adsorption (28.51±0.93 mN/m) of both eugenol-treated and acid-treated liposomes as the energy (1085 J/g) required for the liposomes to reach the interface was much lower than Eugenol-untreated and acid-treated liposomes where the energy was 1743 J/g and the rate of adsorption was (59.89±2.22 mN/m).

Figure 19:
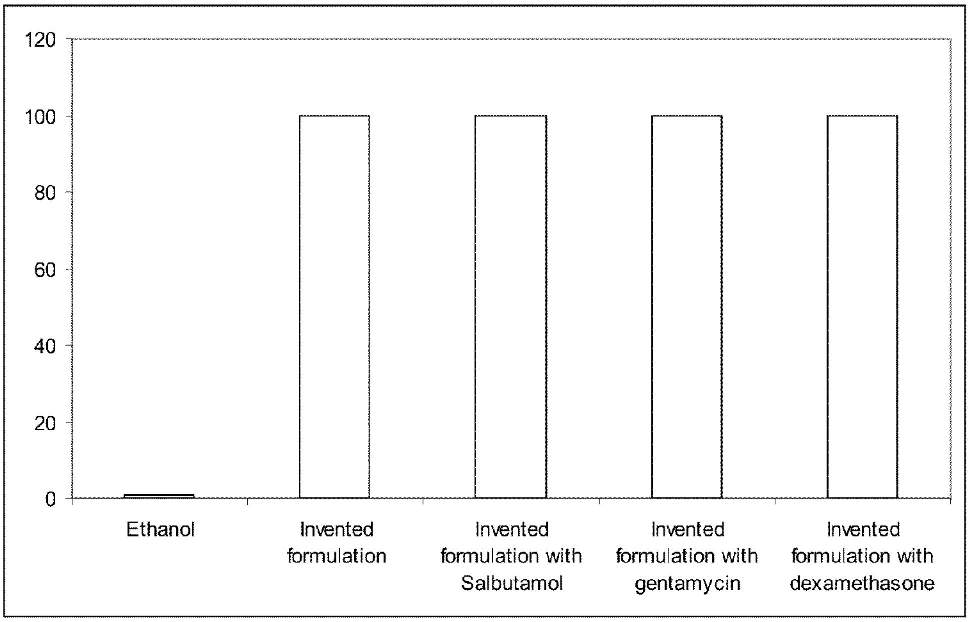
FIG. 19 shows percentage capillary opening: simulation of terminal airway patency

The invented formulation and the drug loaded surfactants maintain 100% airway patency as is reflected in FIG. 19.

Figure 20:
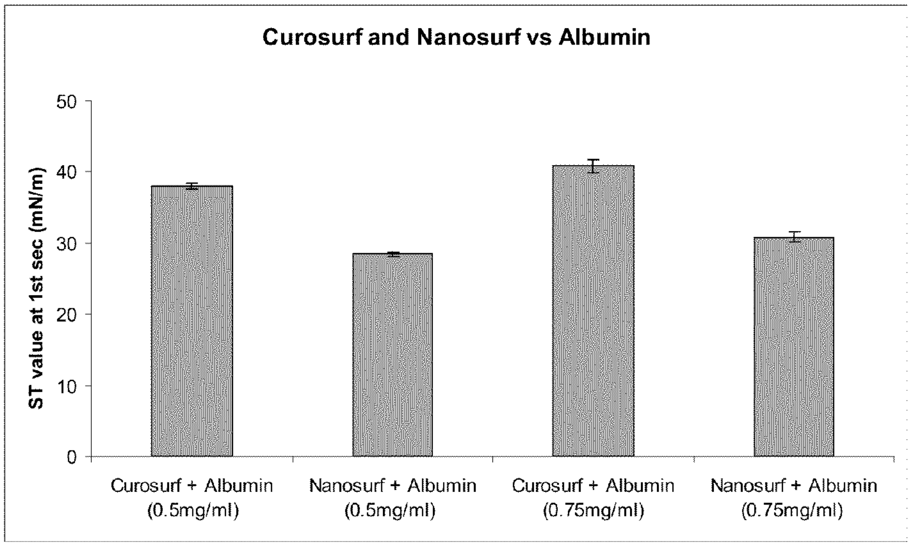
FIG. 20 is an Adsorption Profile: Overcoming inhibitory effects of albumin
Figure 21:
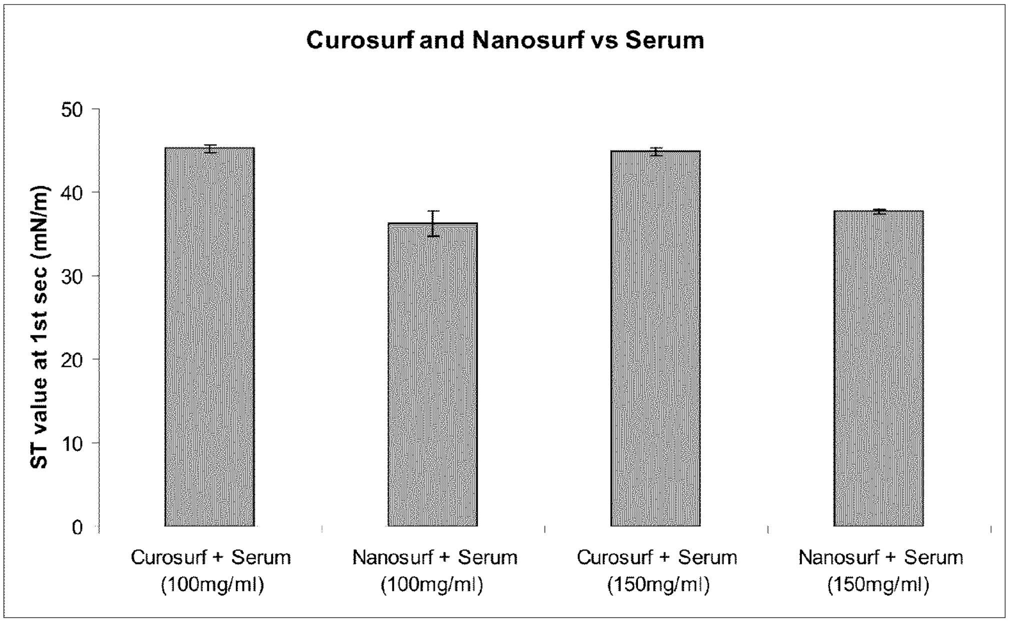
FIG. 21 is an Adsorption Profile: Overcoming inhibitory effects of serum

The invented formulation has statistically significant improvement in surfactant adsorption (28-37 mN/m) to the interface within one second in the presence of inhibitory agents like albumin and serum. This is a great improvement over that of animal derived surfactants like Curosurf. This has implications for ARDS where albumin, serum and fibrinogen are known to flood the alveoli. (FIG. 20, 21).

Figure 22:
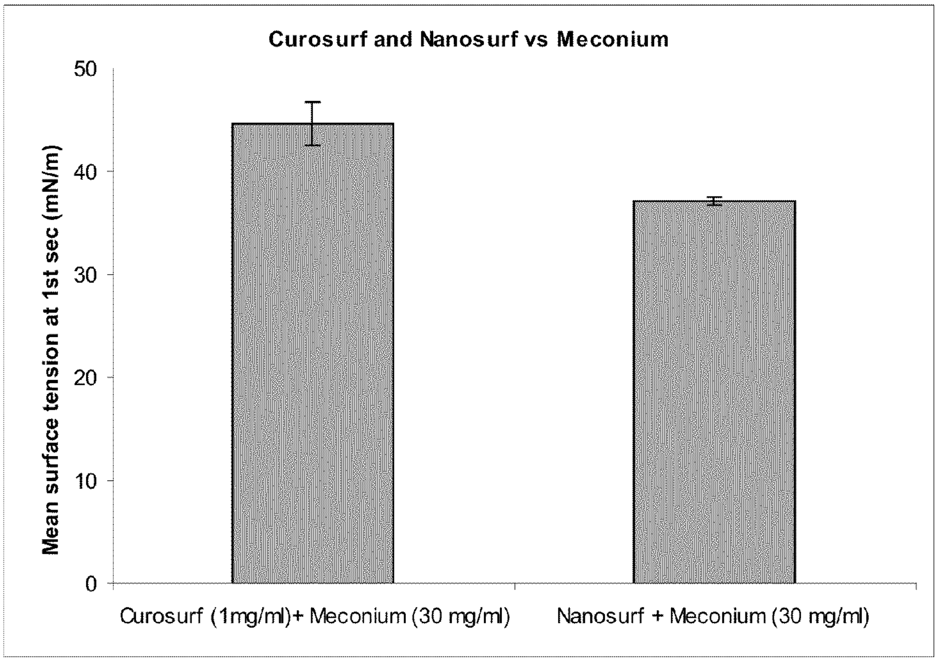
FIG. 22 is an Adsorption Profile: Overcoming inhibitory effects of meconium

The invented formulation has significant improvement in surfactant adsorption (32-39 mN/m) to the interface within, one second in the presence of meconium. This is an improvement over that of animal derived surfactants like Curosurf. This implies the ability of the invented surfactant to overcome adverse interactions of meconium. This has implications for Meconium Aspiration Syndrome where meconium (or the first pass stool of infants) is aspirated by the babies leading to respiratory distress. (FIG. 22).

Figure 23:
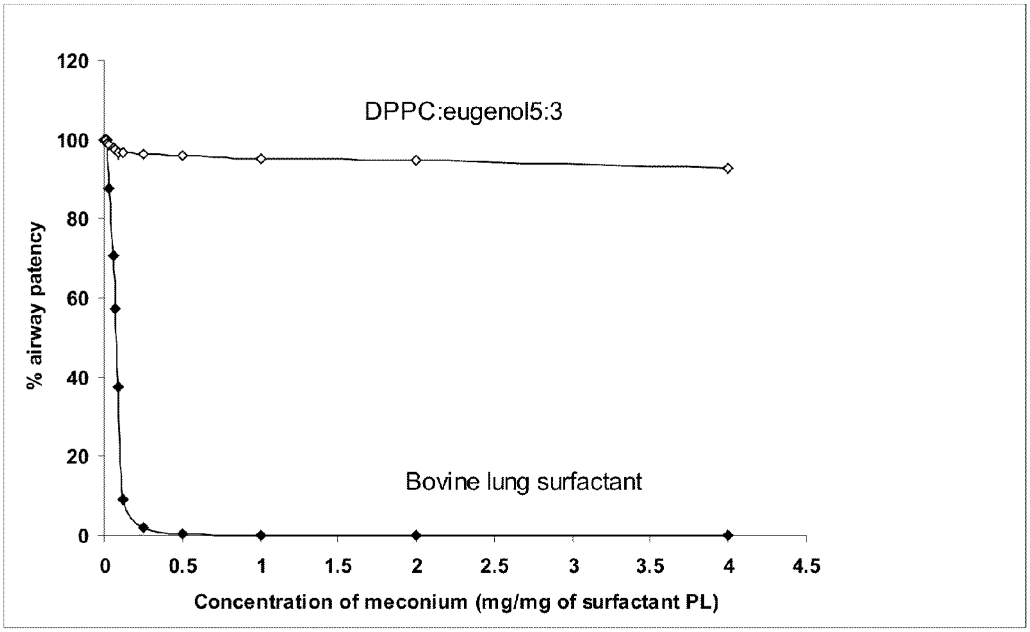
FIG. 23 shows airway patency of DPPC: eugenol 5:3 in the presence of graded amounts of meconium

The invented formulation shows 100% airway patency in the presence of graded amounts of meconium (FIG. 23)

The invented formulation had significant improvement in surfactant adsorption (26-30 mN/m) to the interface within one second in the presence of acids. This is an improvement over that of animal derived surfactants like Curosurf. This implies that the invented formulation overcomes the inhibitory effects of acids. This has implications for acid induced lung injury. This is reflected in FIG. 24.

Figure 25:
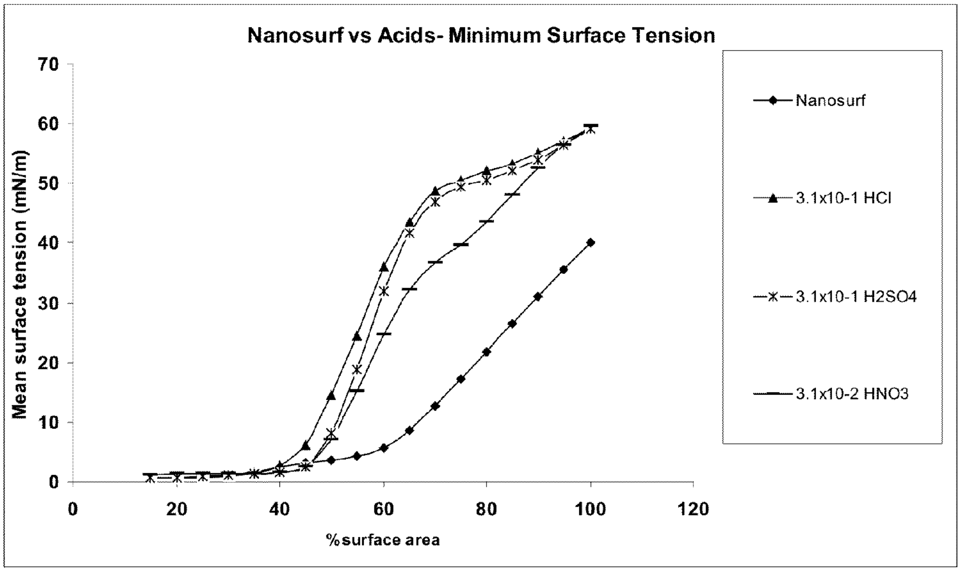
FIG. 25 shows minimum surface tension of invented formulation in presence and absence of acids

The formulation is found to be highly surface active and reaches a low minimum surface tension of ≤2 mN/m even in presence of acids. This is the desired minimum surface tension of natural surfactant. This is reflected in FIG. 25 showing that the surface tension achieved on film compression at 20% area denotes the minimum surface tension. The FIG. 25 depicts that the invented surfactant reaches a surface tension <1 mN/m at a 20% area compression in the presence of all the acids, denoting its superior surfactant function in the presence of acids, in acid injured lungs.

The invented formulation has antioxidant activity without the addition of additional agents like ascorbic acid. The lipid peroxidation of a model unsaturated lipid (soya phosphatidylcholine) was significantly reduced on addition of the surfactant formulation. This is reflected in FIG. 26 wherein the products of lipid peroxidation like malondialdehyde generated by Fenton's reaction are quantified. Soya PC is a representative unsaturated phospholipids known to be susceptible to oxidation.

Figure 27:
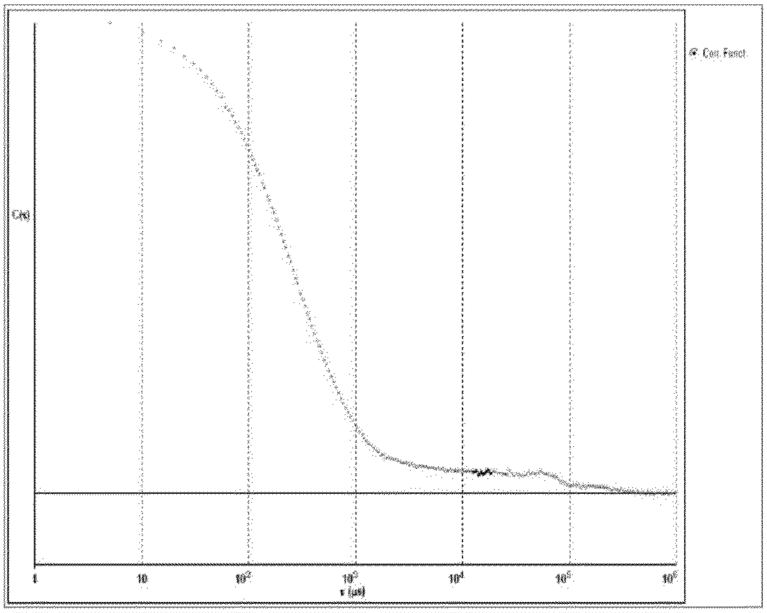
FIG. 27 shows particle sizing: photon correlation spectroscopy data showing nanosized vesicles

The invented formulation has a particle size of about 150-300 nm and forms nanovesicles and networked nanotubes. This is reflected in FIGS. 10 and 27.

Figure 29:
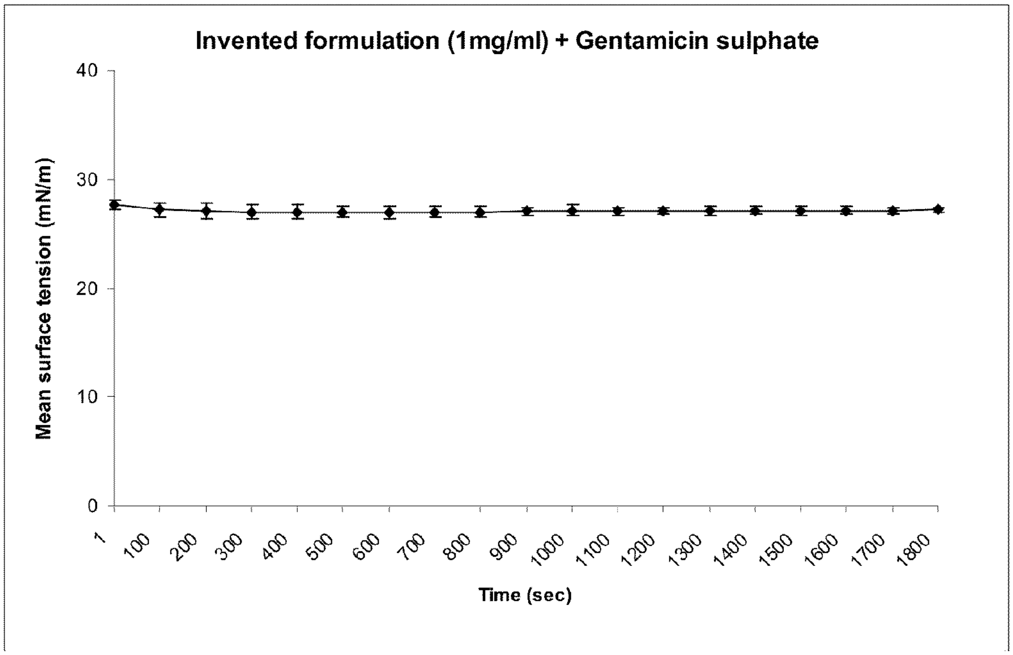
FIG. 29 is an Adsorption Profile of gentamicin loaded surfactant
Figure 30:
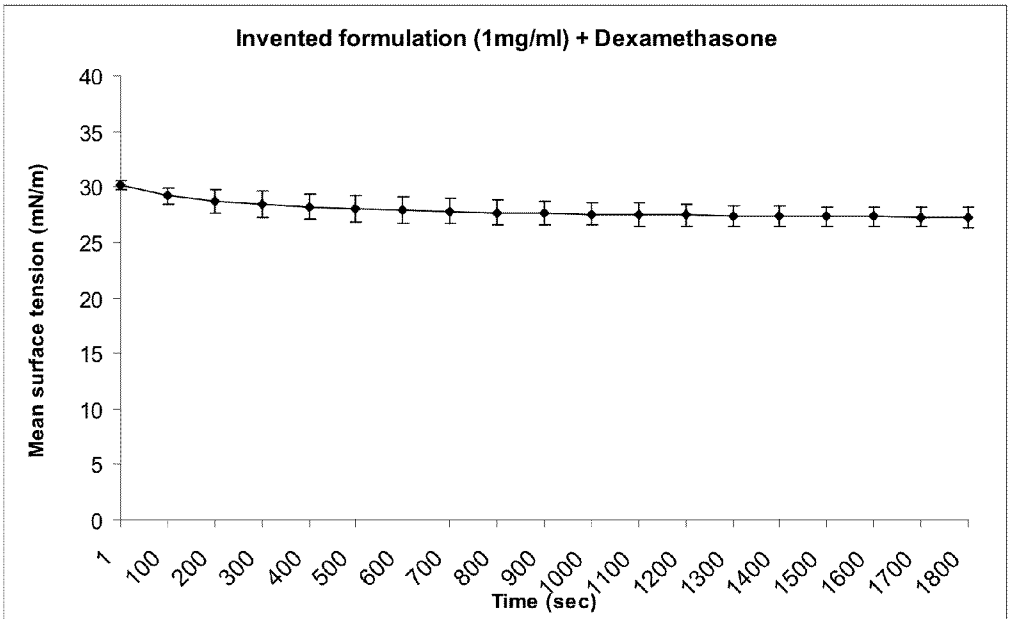
FIG. 30 is an Adsorption Profile of dexamethasone loaded surfactant

In another embodiment, the invented formulation can also be combined with steroidal anti-inflammatory drugs like dexamethasone or bronchodilators like salbutamol or antibiotics like gentamycin. The drug loaded surfactants achieve quick adsorption reaching a surface tension of 28-37 mN/m) to the interface within one second. Salbutamol or dexamethasone is added in a ratio of 1 part of surfactant to 0.1 parts of drug while gentamycin is added in a ratio of 1 part of surfactant to 0.2 parts of drug by weight. The surfactant can act as a carrier for these drugs without adversely affecting the surfactant function. This is reflected in FIGS. 28, 29 and 30.

The invented formulation is safe and non-toxic when administered as an aerosol in a dose of 200 mg/kg as shown in Table 3

TABLE 3

| Acute Inhalation Toxicity | |
|---|---|
| Animal model | Mice |
| Dose of Nanosurf | 200 mg/kg |
| Route | Aerosol |
| Lung weights | No change |
| Animal behavior | Normal, no signs of distress or toxicity |
| Animal weights | Normal, similar to controls |
| Histology | No abnormalities detected |

Figure 31:
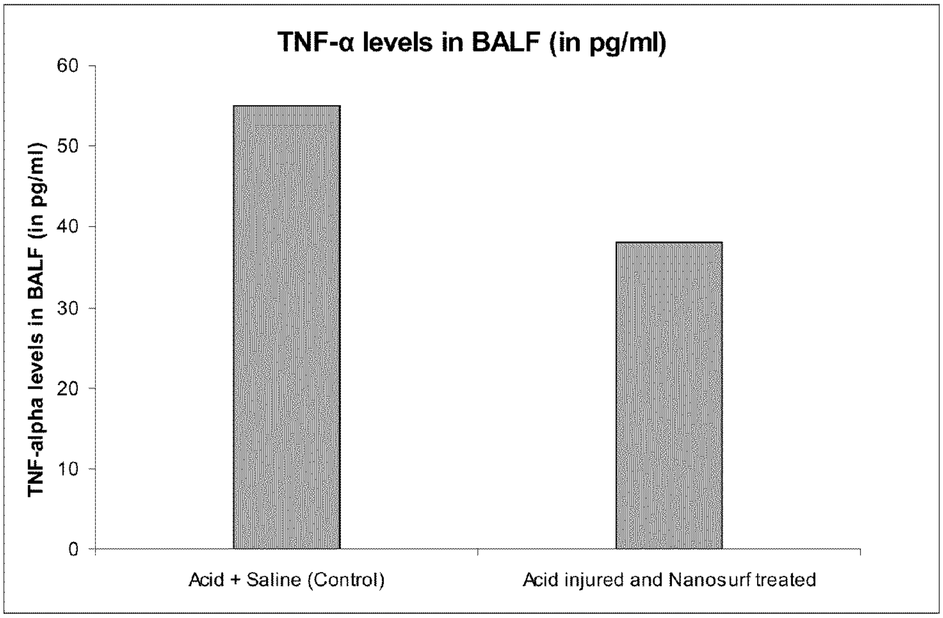
FIG. 31 shows effect of invented surfactant (Nanosurf) on TNF alpha levels in broncoalveolar lavage fluid in acid lung injury
Figure 32:
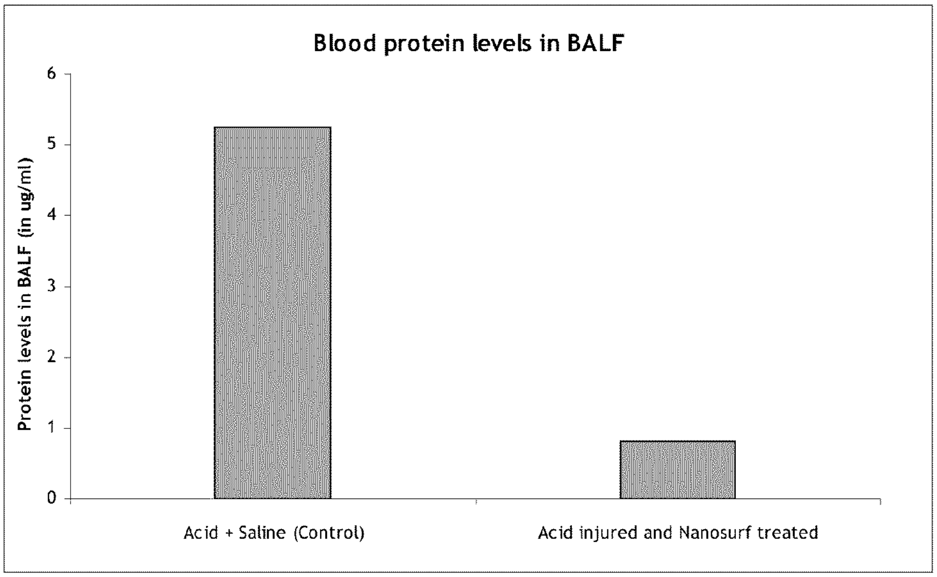
FIG. 32 shows effect of invented surfactant (Nanosurf) on protein leakage in broncholaveolar lavage fluid in acid injured lungs

The invented formulation significantly reduces the protein leakage TNF alpha levels in the bronchoalveolar fluid when nebulised in an acid injured lung (mice model) at a dose of 200 mg/kg. FIG. 31 shows effect of invented surfactant (Nanosurf) on TNF alpha levels in broncoalveolar lavage fluid in acid lung injury. It is seen in FIG. 31 that the inflammatory marker TNFalpha level in the alveolar fluid of acid injured mice is reduced on treating with aerosols of invented formulation. FIG. 32 shows effect of invented surfactant (Nanosurf) on protein leakage in broncholaveolar lavage fluid in acid injured lungs wherein it is seen that the protein leakage in the alveolar fluid of acid injured mice is reduced on treating with aerosols of invented formulation.

Figure 33:
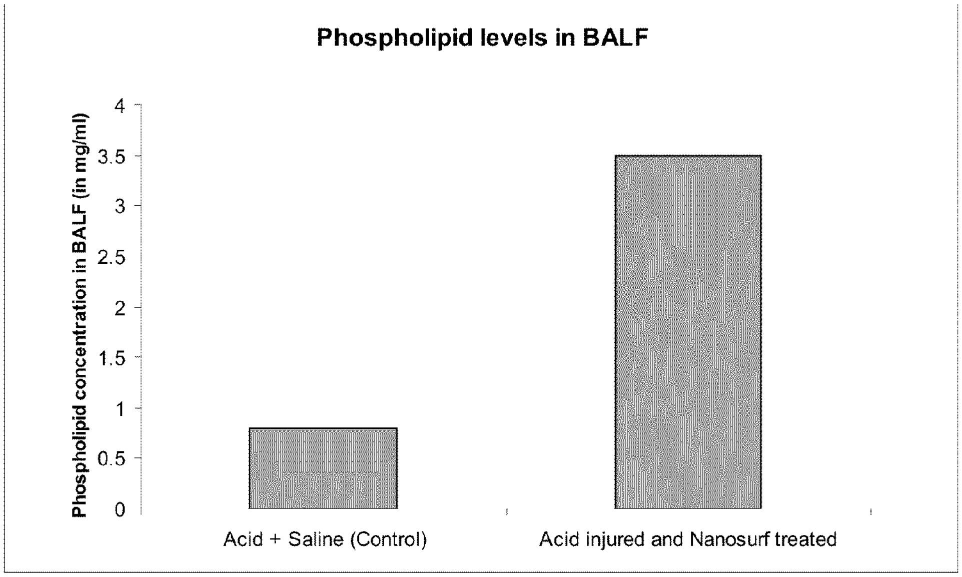
FIG. 33 shows effect of invented surfactant (Nanosurf) on the phospholipid levels in the bronchoalveolar lavage fluid in acid injured lungs
Figure 34:
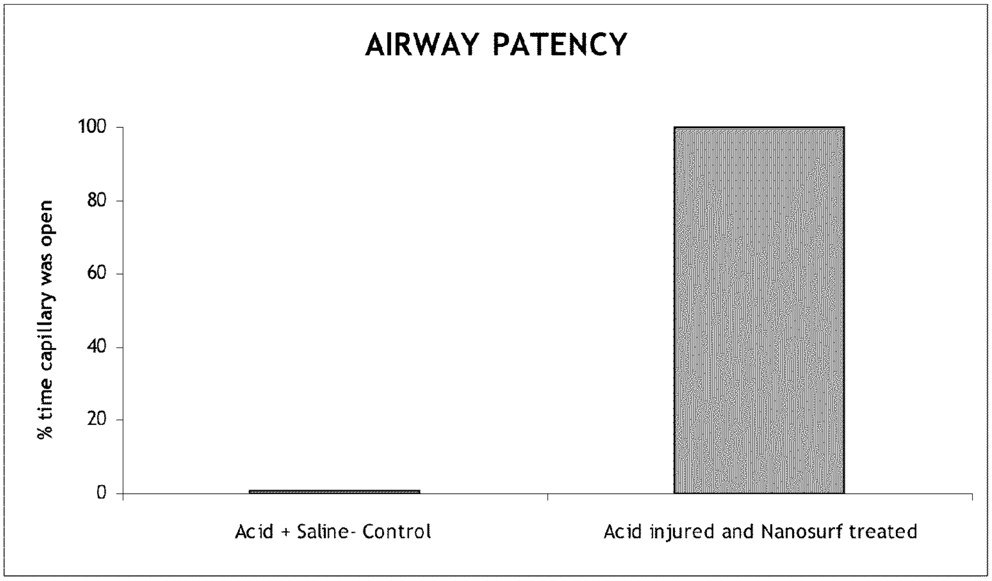
FIG. 34 shows effect of invented surfactant (Nanosurf) on the airway patency of bronchoalveolar lavage fluid in acid injured lungs

The invented formulation significantly increases the airway patency to 100% and the phospholipid levels to 3.5 mg/ml in the bronchoalveolar fluid on nebulisation in an acid injured lung model (in mice) at a dose of 200 mg/kg as compared to the control group treated with saline. (FIG. 33, 34). FIG. 33 shows effect of invented surfactant (Nanosurf) on the phospholipid levels in the bronchoalveolar lavage fluid in acid injured lungs, the phospholipids content of the alveolar fluid of acid injured mice is increased on treating with aerosols of invented formulation.

The invented surfactant reaches a minimum surface tension of <1 mN/m in the absence of any inhibitors and adsorbs quickly to an air-liquid interface to reach a surface tension of 31-32 mN/m within one second. This has implications for surfactant replacement in any surfactant deficiency state like Neonatal Respiratory Distress Syndrome.

TABLE 4

| Surface properties of formulation in absence of inhibitors | |
|---|---|
| Minimum surface tension | ≤1 mN/m |
| Adsorption surface tension at 1 second | 31.5 ± 0.4 mN/m |
| Airway Patency | 100% |

EXAMPLES

The following examples are illustrative of the invention but not limitative of the scope thereof.

Example 1

The invented surfactant formulation (Nanosurf) consists of nanovesicles and networked tubes that are formed by the following method. A desired amount of dipalmitoyl phosphatidylcholine (5 mg) is dissolved with 2:1 chloroform: methanol mixture and a thin film of lipid is made by evaporating the solvent using rotary vacuum evaporator at 40° C. The thin lipid film is then hydrated with hydrating medium composed of 0.9% sodium chloride and 2 mM calcium chloride at pH 7.4 for 1 hour at 45° C. After hydration, eugenol (3 mg) is added and gently mixed. The process spontaneously forms nanovesicles and networked tubes. The addition of eugenol at the end of the hydration period leads to the formation of networked tubes due to surface adsorption. No further sonication or extrusion is required.

Example 2

The invented surfactant (DPPC: eugenol 5:3) achieves 99.8% airway patency in the presence of albumin. This is evaluated in a capillary surfactometer at 37 C at a concentration of 1 mg/ml of the surfactant in the presence of 0.5 mg/ml of albumin. This is superior to the performance of other clove oil and eucalyptus oil added surfactants claimed in prior art. (FIG. 1) D1a consists of DPPC+clove oil+ascorbic acid in the ratio 10:3:0.1 prepared in accordance with Indian Patent 241271. D1b consists of DPPC+eucalyptus oil+ascorbic acid in the ratio 10:3:0.1 prepared in accordance with Indian Patent 241271.

D2a consists of DPPC+eucalyptus oil in a 2:1 ratio in normal saline prepared in accordance with Indian Patent 241272. D2b consists of DPPC+eucalyptus oil in a 1:1 ratio in normal saline prepared in accordance with Indian Patent 241272. DPPC: eugenol5:3 denotes the present invention.

The white bars depict the airway patency of the formulations whereas the grey bars depict the airway patency in the presence of albumin. It is clearly seen that D1a has 0.4% airway opening in presence of albumin, D1b has 6% airway opening in presence of albumin, D2a has 0.3% airway opening in presence of albumin, D2b has 0.2% airway opening in presence of albumin whereas the present invention has 99.8% airway opening in presence of albumin.

Example 3

The invented surfactant (DPPC: eugenol 5:3) has a superior airway patency in the presence of albumin, and in the absence of ascorbic acid, as compared to that of clove oil added surfactants. FIG. 2 compares the airway patency of DPPC:Eugenol 5:3 (present invention) at a concentration of 1 mg/ml with that of DPPC:clove oil 5:3 1 mg/ml in the absence and presence of 0.5 mg/ml of albumin in a capillary surfactometer at 37 C. It is seen that the airway patency of DPPC:

clove oil 5:3 in the presence of albumin is 84.7+/−1.8% whereas the airway patency of DPPC: eugenol 5:3 in the presence of albumin is 99.8=/−0.1%. Further, it is noted that the presence of ascorbic acid is detrimental to the interaction with albumin. The airway patency of DPPC: eugenol :ascorbic acid 5:3:0.1 in the presence of albumin is 2.4+/−0.7% whereas the airway patency of DPPC: eugenol 5:3 in the presence of albumin is 99.8+/−0.1%. Similarly, DPPC:cloveoil:ascorbic acid 5:3:0.1 in the presence of albumin showed an airway patency of 18.8+/−0.9 whereas the airway patency of. DPPC:clove oil 5:3 in the presence of albumin was 84.7=/−1.8% and of DPPC: eugenol 5:3 in the presence of albumin was 99.8+/−0.1%

Example 4

The invented surfactant shows superior airway patency in the presence of albumin, at a specific ratio of 5 parts of dipalmitoylphosphatidylcholine to 3 parts of eugenol in a weight by weight ratio. FIG. 3 depicts this effect. It is seen that the airway patency for DPPC: eugenol 5:3 in a concentration of 1 mg/ml in the presence of 0.5 mg/ml albumin in a capillary surfactometer at 37 C is 99.8=/−0.1% whereas the airway patency of DPPC: eugenol 10:3 in the presence of albumin is 88.2+/−1.3%. Similarly, it is seen that DPPC:clove oil 5:3 in the presence of albumin is 84.8+/−1.8% whereas DPPC:clove oil 10:3 in the presence of albumin is 61.97+/−0.38% whereas the airway patency of DPPC: eugenol 5:3 in the presence of albumin is 99.8+/−0.1%.

Example 5

The invented surfactant shows superior airway patency in the presence of albumin due to synergistic effects of DPPC and eugenol. FIGS. 4,5 and 6 show that DPPC alone shows 0% patency in presence of albumin and eugenol alone shows 0% airway patency in the presence of albumin but surprisingly the DPPC: eugenol combination in a ratio of 5:3 shows 100% airway patency in presence of graded concentrations of albumin in a capillary surfactometer at 37 C.

Example 6

The invented surfactant (DPPC: eugenol 5:3), results in the formation of non-lamellar phases with improved surface activity in the presence of inhibitors. This is depicted by change in laurdan fluorescence and presence of asymmetric $PO_2^-$ stretching vibration band in FTIR spectroscopy. FIG. 7 depicts the Laurdan fluorescence of the invented formulation depicting the formation of non-lamellar phases in the presence of albumin. From FIG. 7 and table 2, The ratio of Laurdan fluorescence in 360 and 390 nm shows that DPPC and DPPC in the presence of albumin give ratios of 2.6 and 1.98 respectively (>1). On the other hand, DPPC: eugenol and DPPC: eugenol in the presence of albumin give laurdan fluorescence in 360 and 390 nm of 0.006 and 0.56 respectively (<1). Similarly, on comparing the fluorescence in 360 and 490 nm, we find that DPPC alone and DPPC in the presence of albumin give ratios of 2.41 and 1.21 respectively (>1). On the other had, DPPC: eugenol and DPPC: eugenol in the presence of albumin give laurdan fluorescence in 360 and 490 nm of 0.003 and 0.077 respectively (<1). Laurdan (6-dodecanoyl-2-dimethylaminonaphthalene) is a fluorescent membrane probe that has the advantage of displaying spectral sensitivity to the phospholipids phase state. Laurdan is located at the hydrophilic-hydrophobic interface of the bilayer and shows sensitivity to the polarity of its environment. Hence, shifts in its spectra can be used to depict membrane perturbations and phase changes. In this case, DPPC: eugenol show a different spectral profile than that of DPPC alone and this is evident even in the presence of albumin. This change in spectra depict the formation of non-lameller phases which is the unique mechanism of the invented surfactant and explains its superior surface activity.

Example 7

The invented surfactant DPPC:Eugenol 5:3 form characteristic bands in FTIR representing non-lamellar phases in the presence of nitric acid. This is inferred by comparing FIGS. 8 and 9. DPPC in the presence of acid gave broad peak ranging from 3439 $cm^{-1}$ to 3460.3 $cm^{-1}$ (indicative of aqueous water, O—H and C—C). Infrared bands characteristic of phosphate group in phospholipids occur in the region 1000-1300 $cm^{-1}$ (indicative of single bond P—O and double bond P═O stretching bands). A sharp peak at 1118 $cm^{-1}$ (characteristic of asymmetric $PO_2^-$ stretching vibration band) was obtained for DPPC liposomes in presence of nitric acid (pH 5). Strong peaks at 1118 $cm^{-1}$ (indicative of symmetric stretch of nitrate ion) for DPPC liposomes were obtained with nitric acid at pH 5 respectively (FIG. 8). This peak shifted to 1209.6 $cm^{-1}$ (characteristic of single bond P—O, double bond P═O stretching and asymmetric $PO_2^-$ stretching vibration bands) in presence of eugenol for DPPC (invented surfactant) with nitric acid (pH 5). This suggests that DPPC: eugenol induced lamellar to non-lamellar phase transition as a result of which the phosphate group showed a shift in the wavenumber. In presence of eugenol, DPPC liposomes treated with nitric acid (pH 5) showed sharp peaks at 1209.6 $cm^{-1}$ (for asymmetric $PO_2^-$ stretching vibration band) and 2849.2 $cm^{-1}$ (indicating symmetric CH2 band). These peaks were not observed in the absence of eugenol. This shift suggests the lamellar to non-lamellar phase transition of DPPC liposomes by eugenol. Presence of asymmetric $PO_2^-$ stretching vibration band indicates the lamellar—$H_{II}$—hexagonal phase transition. The lamellar to non-lamellar phase transition can also be explained by change in the degree of water hydrogen bonding to the phosphate group. (FIG. 9)

Example 8

Figure 26:
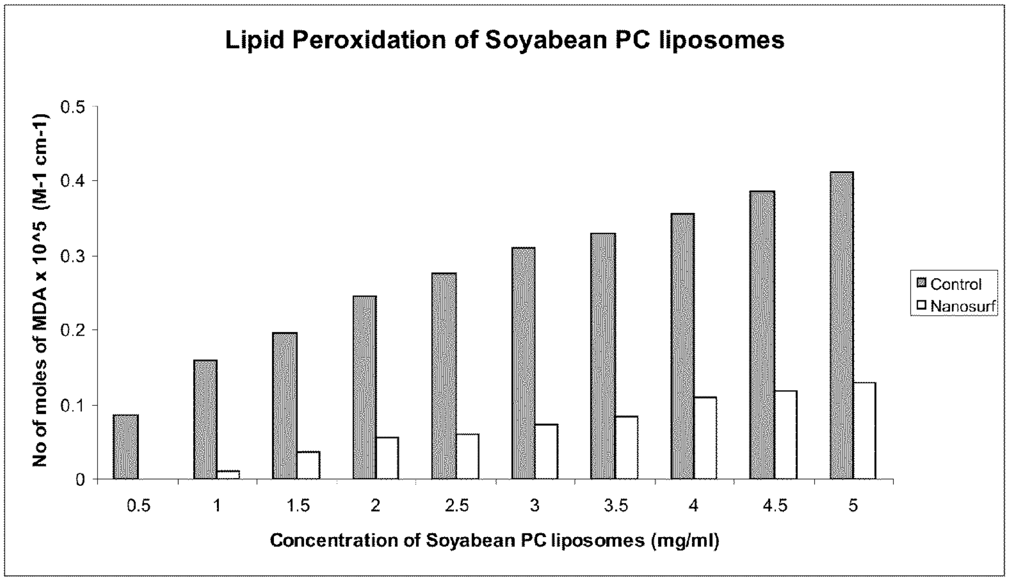
FIG. 26 shows antioxidant effects of invented formulation

The invented surfactant (Nanosurf) spontaneously forms nanovesicles and networked nanotubes as seen in a transmission electron micrograph of the invented surfactant shown in FIG. 10. The average size of the nanostructures as depicted by photon correlation spectroscopy show a diameter of 226 nm (FIG. 26).

Example 9

The invented surfactant of DPPC: eugenol 5:3 forms closely packed structures having nanodomains in the presence of albumin. The DPPC: eugenol surfactant in the absence and presence of albumin was compared with that of DPPC alone in the absence and presence of albumin, using atomic force microscopy (AFM). AFM images of DPPC in the presence of albumin and DPPC: eugenol 5:3 in the presence of albumin are depicted in FIGS. 11 and 13 respectively and the roughness of the structures are depicted in FIGS. 12 and 14. FIG. 11 of DPPC in the presence of albumin shows large aggregates of 540-550 nm sized domains whereas in FIG. 13 of DPPC: eugenol in the presence of albumin clearly defined closely packed domains of 80-90 nm. The surface roughness of DPPC in the presence of albumin is depicted in FIG. 12. It confirms large aggregates with roughness of 47.47 nm. On the other hand, in the case of DPPC: eugenol in the presence of albumin, the surface roughness is only 8.9 nm as depicted in FIG. 14. The formation of nanodomains of 80-90 nm with surface roughness of 8.9 nm allows a closely packed organization which accounts for the improved surface activity of the surfactant in the presence of albumin.

Example 10

Figure 17:
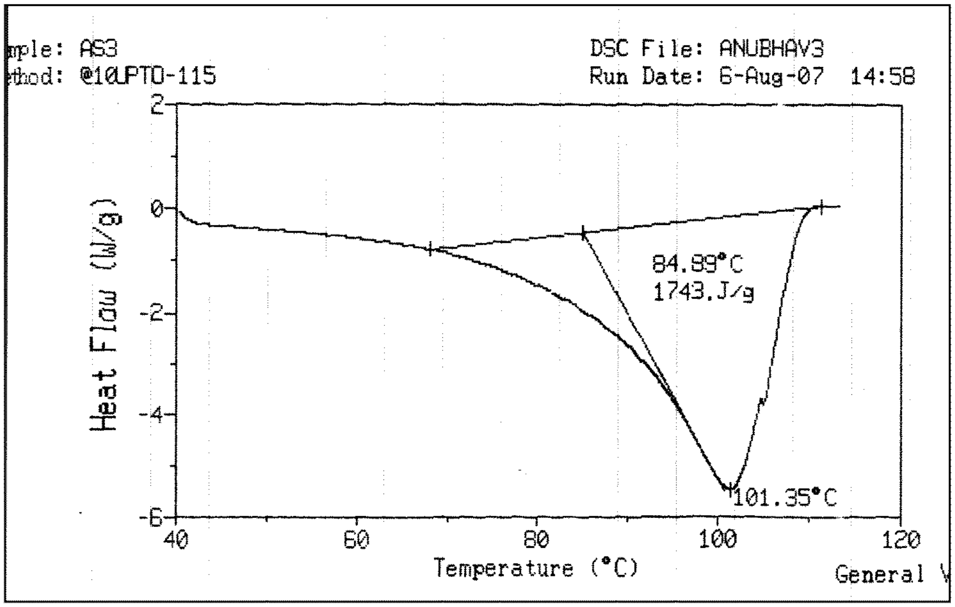
FIG. 17 is a Thermogram of DPPC liposomes (1 mg/ml) and HCl ($3.1\times10^{-1}$ moles/$dm^3$)
Figure 18:
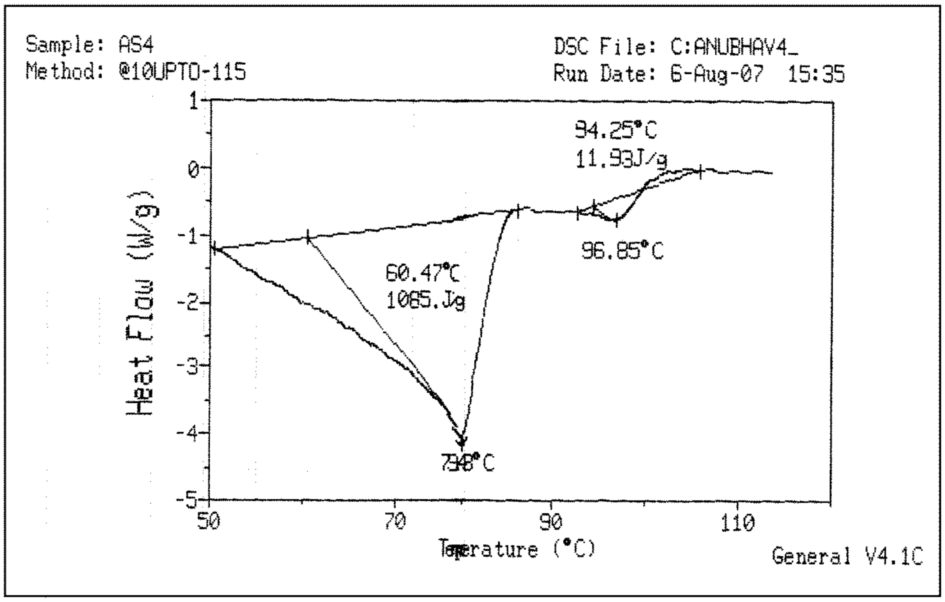
FIG. 18 is a Thermogram of DPPC liposomes (1 mg/ml) and HCl ($3.1\times10^{-1}$ moles/$dm^3$) and Eugenol

The invented surfactant DPPC: eugenol 5:3 decreases the activation energy for adsorption in the presence of acids as seen by comparing FIGS. 15, 16, 17 and 18. By lowering the energy barrier, the rate of adsorption of DPPC: eugenol is greatly enhanced. Differential scanning calorimetry (DSC) was used to study the interaction of bioactive compounds with model lipid bilayers such as DPPC. The experiments were performed at temperature ranging from 35° C. to 115° C. The rate of heating was 3° C./min and the system was allowed to cool to about 35° C. before the next experiment. DSC results proved that there was a change in the energy required by the nanoveesicles to reach the interface for adsorption and The unique combination of DPPC: eugenol 5:3 reduces this energy required by the nanovesicles to reach the interface and thereby enhances the rate of adsorption. The lower the energy required by the nanovesicles, better is the rate of adsorption. FIGS. 15 and 17 showed that for DPPC liposomes, there was a large energy requirement (1325 J/g) of acid-untreated liposomes to reach the interface which slowed down the rate of adsorption (44.66±1.71mN/m). On addition of HCl (as an acid inhibitor), there was an increase in the energy (1743 J/g) of the DPPC liposomes which affected the adsorption (59.89±2.22mN/m) of these acid-treated liposomes. The energy barrier prevented the rapid entry of these liposomes at the interface thereby affecting adsorption. On the other hand, the invented formulation of DPPC: eugenol showed a lower energy requirement of 1079 J/g which was associated with an improved adsorption (31.49±0.43mN/m) (FIG. 16). Similarly, even in the acid-treated state, the DPPC: eugenol 5:3 showed a low energy requirement of 1085 J/g required for the liposomes to reach the interface which was associated with an improved adsorption (FIG. 18).

Example 11

The invented formulation DPPC: eugenol 5:3 (Nanosurf) as well as DPPC: eugenol 5:3 along with the drugs gentamycin, dexamethasone or salbutamol showed 100% airway patency when evaluated in a capillary surfactometer at a concentration of 1 mg/ml at 37 C. (FIG. 19)

Example 12

The invented surfactant formulation DPPC: eugenol 5:3 (referred to as Nanosurf) had statistically significant improvement in surfactant adsorption (28-37 mN/m) to the interface within one second in the presence of inhibitory agents like albumin and serum, when evaluated in a langmuir trough at 37 C at a surfactant concentration of 1 mg/ml. This is an improvement over that of animal derived surfactants like Curosurf. This has implications for ARDS where albumin, serum and fibrinogen are known to flood the alveoli. (FIG. 20, 21).

Example 13

The invented surfactant formulation DPPC: eugenol 5:3 (referred to as Nanosurf) had significant improvement in surfactant adsorption (32-39 mN/m) to the interface within one second in the presence of meconium, when evaluated in a langmuir trough at 37 C at a surfactant concentration of 1 mg/ml. This is an improvement over that of animal derived surfactants like Curosurf. This implies the ability of the invented surfactant to overcome adverse interactions of meconium. This has implications for Meconium Aspiration Syndrome where meconium (or the first pass stool of infants) is aspirated by the babies leading to respiratory distress. (FIG. 22).

Example 14

The invented surfactant formulation DPPC: eugenol 5:3 showed 100% airway patency in the presence of graded amounts of meconium when evaluated in a capillary surfactometer at a concentration of 1 mg/ml of surfactant and 1-30 mg/ml of meconium. The boc\vine lung surfactant (an animal derived commercial surfactant showed low airway patency in the presence of meconium. (FIG. 23).

Example 15

Figure 24:
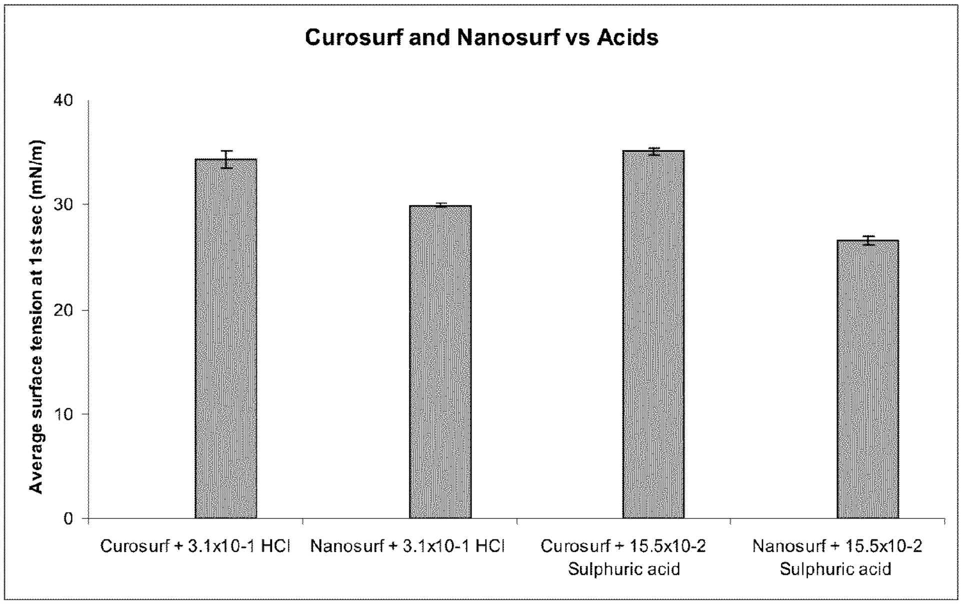
FIG. 24 is an Adsorption Profile: Overcoming inhibitory effects of acids

The invented surfactant formulation DPPC: eugenol 5:3 (referred to as Nanosurf) had significant improvement in surfactant adsorption (26-30 mN/m) to the interface within one second in the presence of acids when evaluated in a langmuir trough at 37 C at a surfactant concentration of 1 mg/ml. This is an improvement over that of animal derived surfactants like Curosurf. This implies that the invented formulation overcomes the inhibitory effects of acids. This has implications for acid induced lung injury. (FIG. 24).

Example 16

The invented surfactant DPPC: eugenol 53 (Nanosurf) formed monolayers that reached a low minimum surface tension of ≤2 mN/m even in presence of acids. The monolayers were evaluated as spread films in a Langmuir Blodgett trough at 37 C and were compressed at a rate of 120 mm/min. The surface tension at 20% film area (left end of the curves) is designated as the minimum surface tension and is found to be the same low value of <2 mN/m in the absence and presence of acids. This is the desired minimum surface tension of natural surfactant. This suggests that the surfactant is effective in the presence of acid inhibitors seen in acid lung injury (FIG. 25).

Example 17

The invented surfactant formulation DPPC: eugenol 5:3 (Nanosurf) has antioxidant activity without the addition of additional agents like ascorbic acid. The lipid peroxidation of a model unsaturated lipid (soya phosphatidylcholine) was significantly reduced on addition of the surfactant formulation. This is seen as a reduction in the products of lipid peroxidation like malondialdehyde generated by Fenton's reaction which are quantified. Soya phosphatidylcholine is a representative unsaturated phospholipid known to be susceptible to oxidation (FIG. 26)

Example 18

Figure 28:
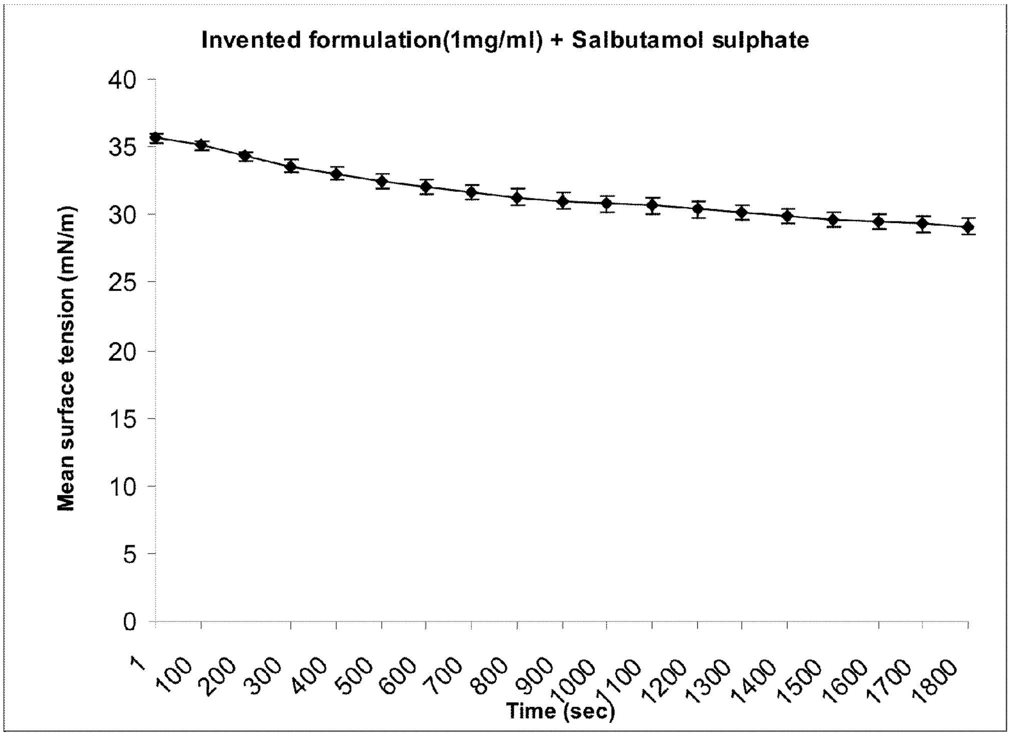
FIG. 28 is an Adsorption Profile of salbutamol loaded surfactant

The invented surfactant formulation (DPPC: eugenol 5:3, referred to as Nanosurf) when combined with steroidal anti-inflammatory drugs like dexamethasone or bronchodilators like salbutamol or antibiotics like gentamycin showed quick adsorption reaching a surface tension of 28-37 mN/m) to the interface within one second at 37 C in a langmuir trough at a surfactant concentration of 1 mg/ml. Salbutamol or dexamethasone were added in a ratio of 1 part of surfactant to 0.1 parts of drug while gentamycin was added in a ratio of 1 part of surfactant to 0.2 parts of drug by weight. The surfactant can act as a carrier for these drugs without adversely affecting the surfactant function (FIG. 28, 29, 30)

Example 19

The invented surfactant formulation was found to be safe and non-toxic when administered as an aerosol in a dose of 200 mg/kg to mice. All physiological parameters were found to be normal when evaluated over a seven day period. (Table 1)

Example 20

The invented surfactant formulation (DPPC: eugenol 5:3) referred to as Nanosurf significantly reduced the protein leakage and TNF alpha levels in the bronchoalveolar fluid when nebulised in an acid injured lung (mice model) at a dose of 200 mg/kg. The control group received acids and were treated with saline alone. (FIG. 31, 32)

Example 21

The invented surfactant formulation (DPPC: eugenol 5:3) referred to as Nanosurf significantly increased the airway patency to 100% and the phospholipid level to 3.5 mg/ml in the bronchoalveolar fluid on nebulisation in an acid injured lung model (in mice) at a dose of 200 mg/kg is compared to the control group treated with saline. (FIG. 33, 34)

Example 22

The invented surfactant DPPC: eugenol 5:3 reaches a minimum surface tension of <1 mN/m in the absence of any inhibitors and adsorbs quickly to an air-liquid interface to reach a surface tension of 31-32 mN/m within one second. This has implications for surfactant replacement in any surfactant deficiency state like Neonatal Respiratory Distress Syndrome. (Table 3)

The invention claimed:

1. A protein free surfactant composition comprising dipalmitoylphosphatidyl choline (DPPC) and eugenol having a weight ratio of DPPC to eugenol in a range of 10:5 to 4:2 with 99-100% airway patency in the presence of at least one member of the group consisting of albumin, serum, and acid, wherein there is an absence of ascorbic acid, for treating at least one disease of the group consisting of acid lung injury, adult respiratory distress syndrome and meconium aspiration syndrome, the composition having an absence of clove oil.

2. A composition as claimed in claim 1, wherein DPPC and eugenol are in a weight ratio of 5:3.

3. The composition as claimed in claim 1, in a form of nanovesicles and net worked nanotubes having a particle size of 150-300 nm.

4. The composition as claimed in claim 1, wherein the composition forms non-lamellar phases in the presence of albumin and acid.

5. The composition as claimed in claim 1, forms closely packed domains of 75 nm with roughness of 9 nm in the presence of albumin.

6. The composition as claimed in claim 1, adsorbs to the air-liquid interface, in the presence of albumin to an adsorption surface tension of 28-37 mN/m within 1 second.

7. The composition as claimed in claim 1, having 99-100% airway patency in the presence of albumin or serum.

8. The composition as claimed in claim 1, having 99-100% airway patency in the presence of acid.

9. The composition as claimed in claim 1, capable of adsorbing to the air-liquid interface, in the presence of acids at an adsorption surface tension of 26-30 mN/m within 1 second.

10. The composition as claimed in claim 1, having 99-100% airway patency in the presence of meconium.

11. The composition as claimed in claim 1, capable of adsorbing to the air-liquid interface, in the presence of meconium at an adsorption surface tension of 32-39 mN/m within 1 second.

12. The composition as claimed in claim 2, when nebulised at a dose of 200 mg/kg, shows TNF alpha values of 30-40 pg/ml in the bronchoalveolar fluid in acid lung injury.

13. The composition as claimed in claim 2, when nebulised at a dose of 200 mg/kg, shows low protein levels of 1-2 microgram/ml in the bronchoalveolar fluid in acid lung injury.

14. The composition as claimed in claim 2, when nebulised at a dose of 200 mg/kg, shows high airway patency of 99-100% in the bronchoalveolar fluid in acid lung injury.

15. The composition as claimed in claim 1, wherein the surface tension of composition on film compression in the absence or presence of acids is 0-2 mN/m.

16. The composition as claimed in claim 1, in the form of nanovesicles and networked tubes 100-250 nm in size.

17. The composition as claimed in claim 1, maintains 100% airway patency when delivered along with dexamethasone, gentamycin or salbutamol.

18. The composition as claimed in claim 1, in combination with steroidal anti-inflammatory drugs, bronchodilators or antibiotics.

19. A process for producing a protein-free pulmonary surfactant composition of claim 1 comprising the steps of:

preparing a solution of DPPC in an organic solvent;

drying the solution of DPPC to form a thin film under vacuum in a rotary vacuum evaporator at 40° C.;

adding 0.9% normal saline containing 2 mM calcium chloride at a pH 7.4 and hydrating the thin film for a period of 1 hour at 45° C.;

adding eugenol in order to obtain a weight ratio of DPPC to eugenol in a range of 10:5 to 4:2, after hydration to form eugenol surface adsorbed nanovesicles and networked tubes.

20. The composition as claimed in claim 2, having a particle size of 150-300 nm in the form of nanovesicles and networked nanotubes.

21. The composition as claimed in claim 2, consisting essentially of DPPC and eugenol.

22. The composition as claimed in claim 21, having a particle size of 150-300 nm in the form of eugenol surface adsorbed nanovesicles and networked tubes.

23. A process as claimed in claim 19, wherein the weight ratio of DPPC to eugenol is 5:3.

* * * * *